(12) United States Patent
Neary et al.

(10) Patent No.: US 9,572,684 B2
(45) Date of Patent: Feb. 21, 2017

(54) INTERBODY INSERTION TOOL AND METHOD

(71) Applicant: INNOVASIS, INC., Salt Lake City, UT (US)

(72) Inventors: Douglas Wayne Neary, Santa Ana, CA (US); Jeffrey Eugene Deckey, Newport Coast, CA (US); Gerald John Alexander, Irvine, CA (US); Roger Denis Sung, Colorado Springs, CO (US)

(73) Assignee: Innovasis, Inc., Salt Lake City, UT (US)

( * ) Notice: Subject to any disclaimer, the term of this patent is extended or adjusted under 35 U.S.C. 154(b) by 75 days.

(21) Appl. No.: 14/137,217

(22) Filed: Dec. 20, 2013

(65) Prior Publication Data

US 2014/0188226 A1    Jul. 3, 2014

Related U.S. Application Data

(60) Provisional application No. 61/745,922, filed on Dec. 26, 2012.

(51) Int. Cl.
| | | |
|---|---|---|
| *A61B 17/70* | (2006.01) | |
| *A61F 2/46* | (2006.01) | |
| *A61F 2/44* | (2006.01) | |

(52) U.S. Cl.
CPC ............ *A61F 2/4611* (2013.01); *A61F 2/4455* (2013.01); *A61F 2002/4623* (2013.01); *A61F 2002/4627* (2013.01); *A61F 2002/4629* (2013.01)

(58) Field of Classification Search
CPC ............ A61F 2/44; A61F 2/441; A61F 2/442; A61F 2/46; A61F 2/4601; A61F 2/4603; A61F 2/4611; A61F 2/4611; A61F 2002/442; A61F 2002/4475; A61F 2002/4495; A61F 2002/46; A61F 2002/4601; A61F 2002/4603; A61F 2002/4627; A61F 2002/444; A61F 17/3468; A61F 17/7097; A61F 17/7098; A61F 17/88; A61F 17/8802; A61F 17/8805; A61F 17/8819; A61F 17/8822; A61F 17/8825; A61F 17/8841; A61F 17/885; A61F 17/8852; A61F 17/8855; A61F 17/8858; A61F 17/3443

See application file for complete search history.

(56) References Cited

U.S. PATENT DOCUMENTS

| | | | |
|---|---|---|---|
| 5,569,247 A | 10/1996 | Morrison | |
| 5,683,391 A | 11/1997 | Boyd | |
| 5,772,661 A | 6/1998 | Michelson | |
| 6,033,405 A * | 3/2000 | Winslow | ............... A61B 17/861 606/86 R |
| 6,156,037 A | 12/2000 | LeHuec et al. | |
| 6,896,676 B2 * | 5/2005 | Zubok et al. | ................. 606/914 |
| 7,452,369 B2 | 11/2008 | Barry | |
| 7,655,046 B2 | 2/2010 | Dryer et al. | |
| 8,048,084 B2 * | 11/2011 | Schneid | .......................... 606/99 |
| 8,273,126 B2 * | 9/2012 | Lindner | ..................... 623/17.15 |

(Continued)

*Primary Examiner* — Lynnsy Summitt
(74) *Attorney, Agent, or Firm* — Workman Nydegger

(57) ABSTRACT

An interbody insertion tool and cage for use during an interbody spinal fusion procedure is disclosed. In one aspect, the tool comprises a rod centrally located within the tool that has the ability to remain attached to the cage to aid in: coupling the tool to the cage, release of the tool from the cage, alignment of additional hardware, and insertion of materials within the hollow of the cage.

15 Claims, 27 Drawing Sheets

(56) References Cited

U.S. PATENT DOCUMENTS

| | | | |
|---|---|---|---|
| 8,465,546 B2* | 6/2013 | Jodaitis et al. | 623/17.16 |
| 8,491,655 B2* | 7/2013 | Adamo | 623/17.14 |
| 8,518,087 B2* | 8/2013 | Lopez et al. | 606/279 |
| 8,579,910 B2* | 11/2013 | Hester et al. | 606/99 |
| 2002/0138146 A1 | 9/2002 | Jackson | |
| 2008/0312742 A1 | 12/2008 | Abernathie | |
| 2009/0012529 A1* | 1/2009 | Blain et al. | 606/99 |
| 2009/0030421 A1* | 1/2009 | Hawkins et al. | 606/99 |
| 2009/0248164 A1 | 10/2009 | Sweeney | |
| 2010/0179594 A1* | 7/2010 | Theofilos | A61F 2/447 606/247 |
| 2010/0280619 A1* | 11/2010 | Yuan | A61B 17/1671 623/17.16 |
| 2010/0292800 A1* | 11/2010 | Zubok | 623/17.16 |
| 2011/0077740 A1* | 3/2011 | Perez-Cruet | A61F 2/4455 623/17.16 |
| 2011/0218582 A1* | 9/2011 | Smith | A61B 17/56 606/86 R |
| 2011/0218583 A1* | 9/2011 | Smith | A61B 17/56 606/86 R |
| 2011/0301612 A1* | 12/2011 | Richter et al. | 606/99 |
| 2014/0249636 A1* | 9/2014 | Bouchot et al. | 623/17.16 |

* cited by examiner

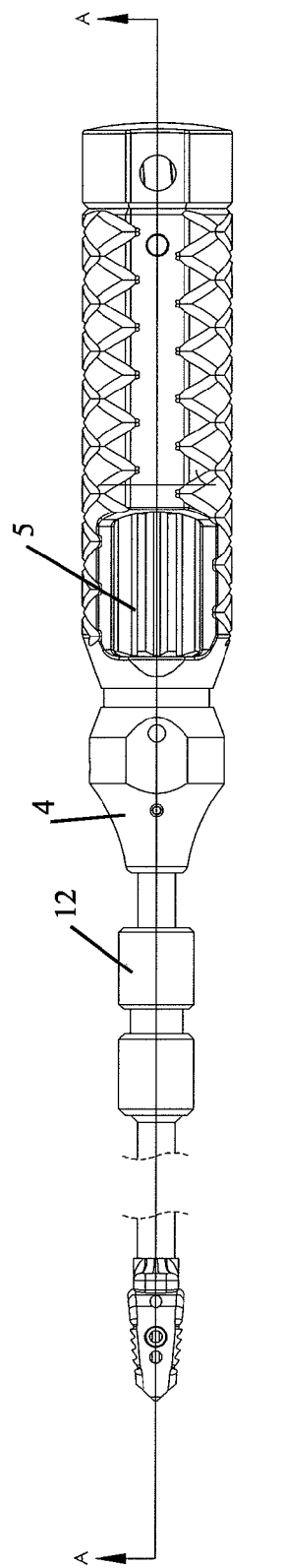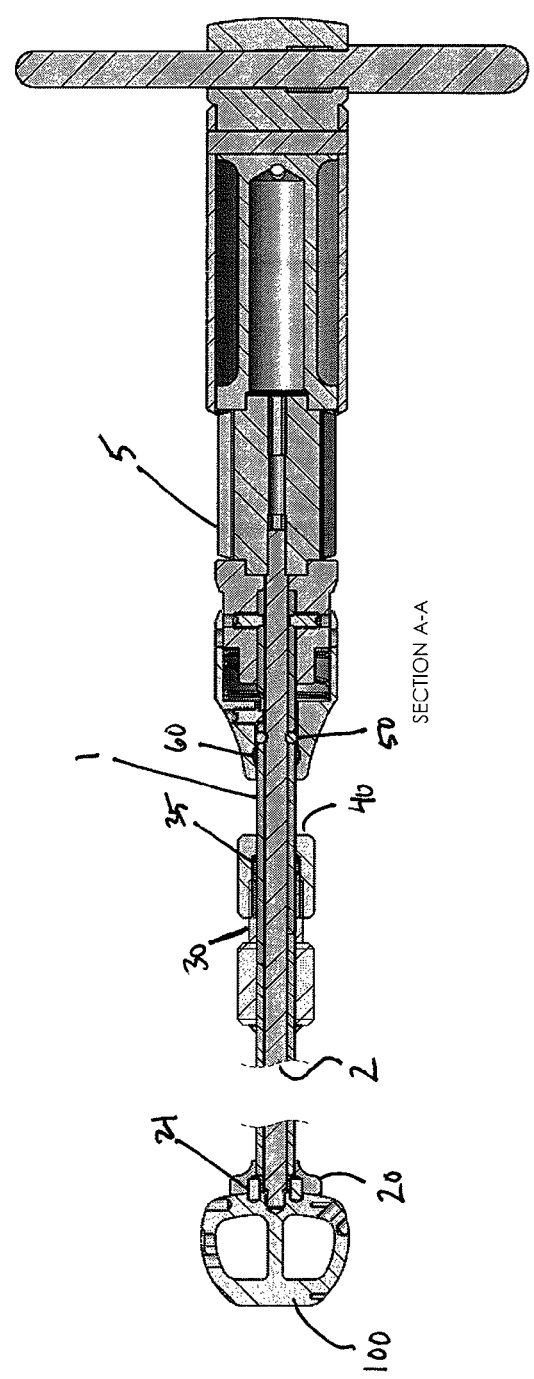
Figure 3A
Figure 3B

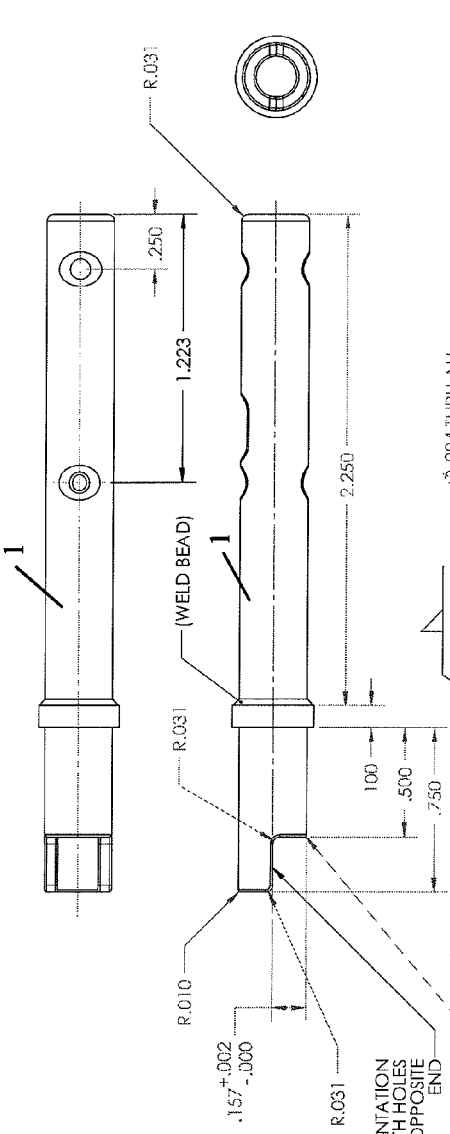
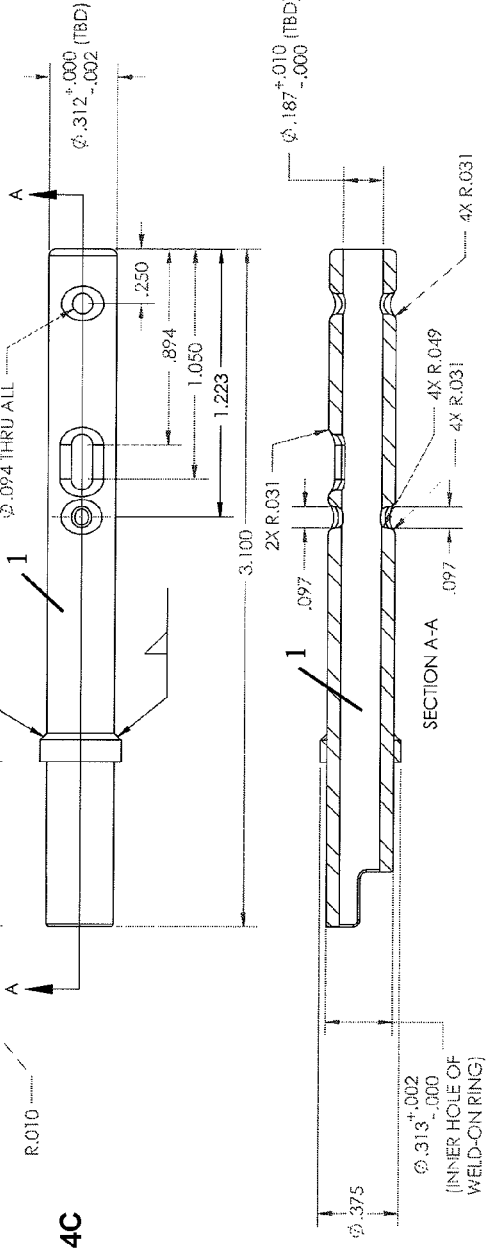
Figure 4A
Figure 4B
Figure 4C
Figure 4D

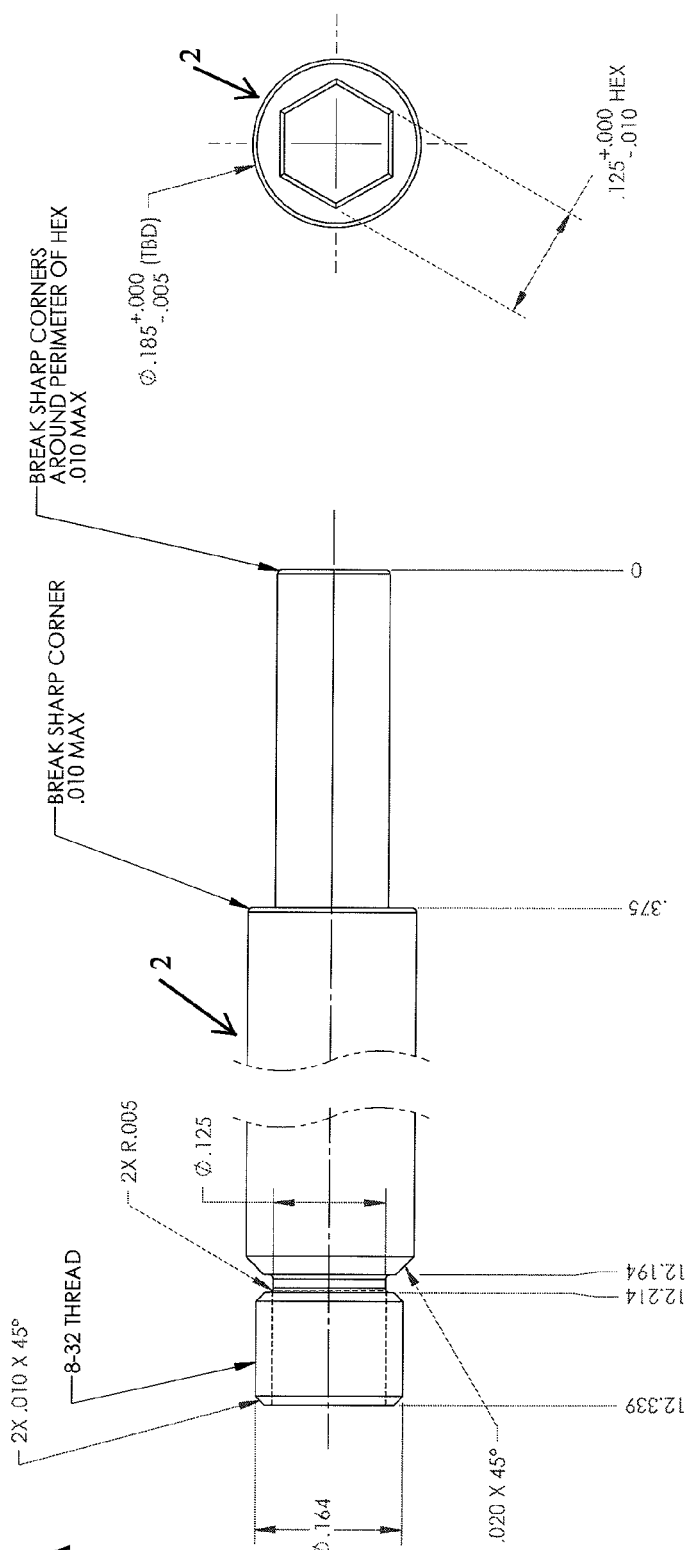

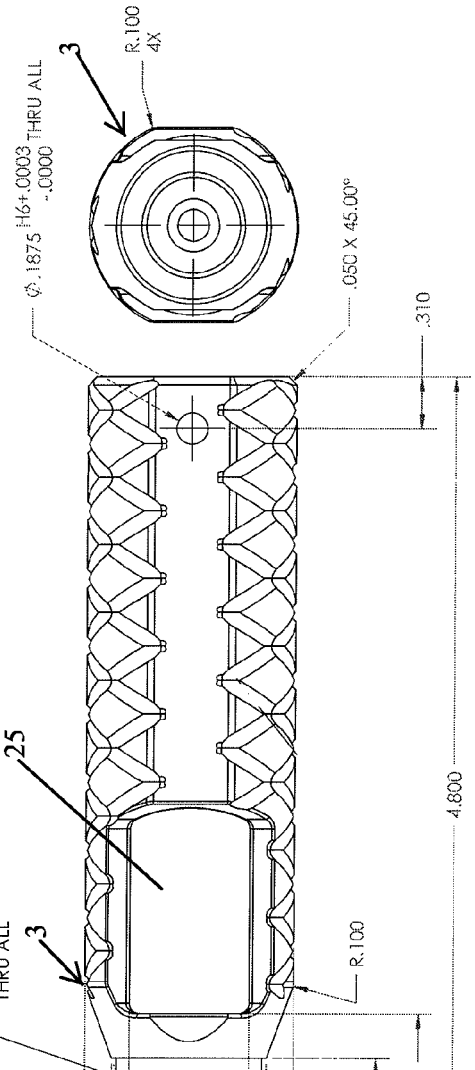
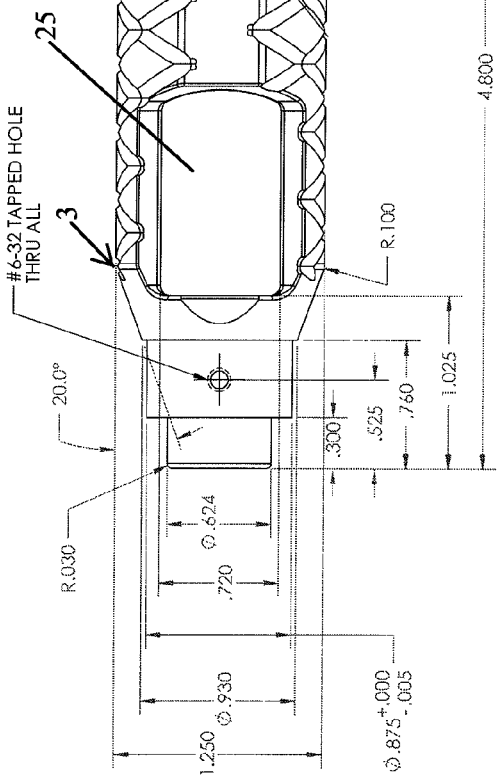
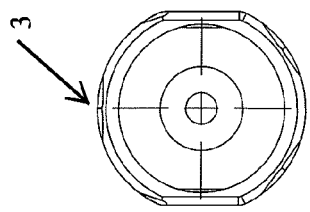

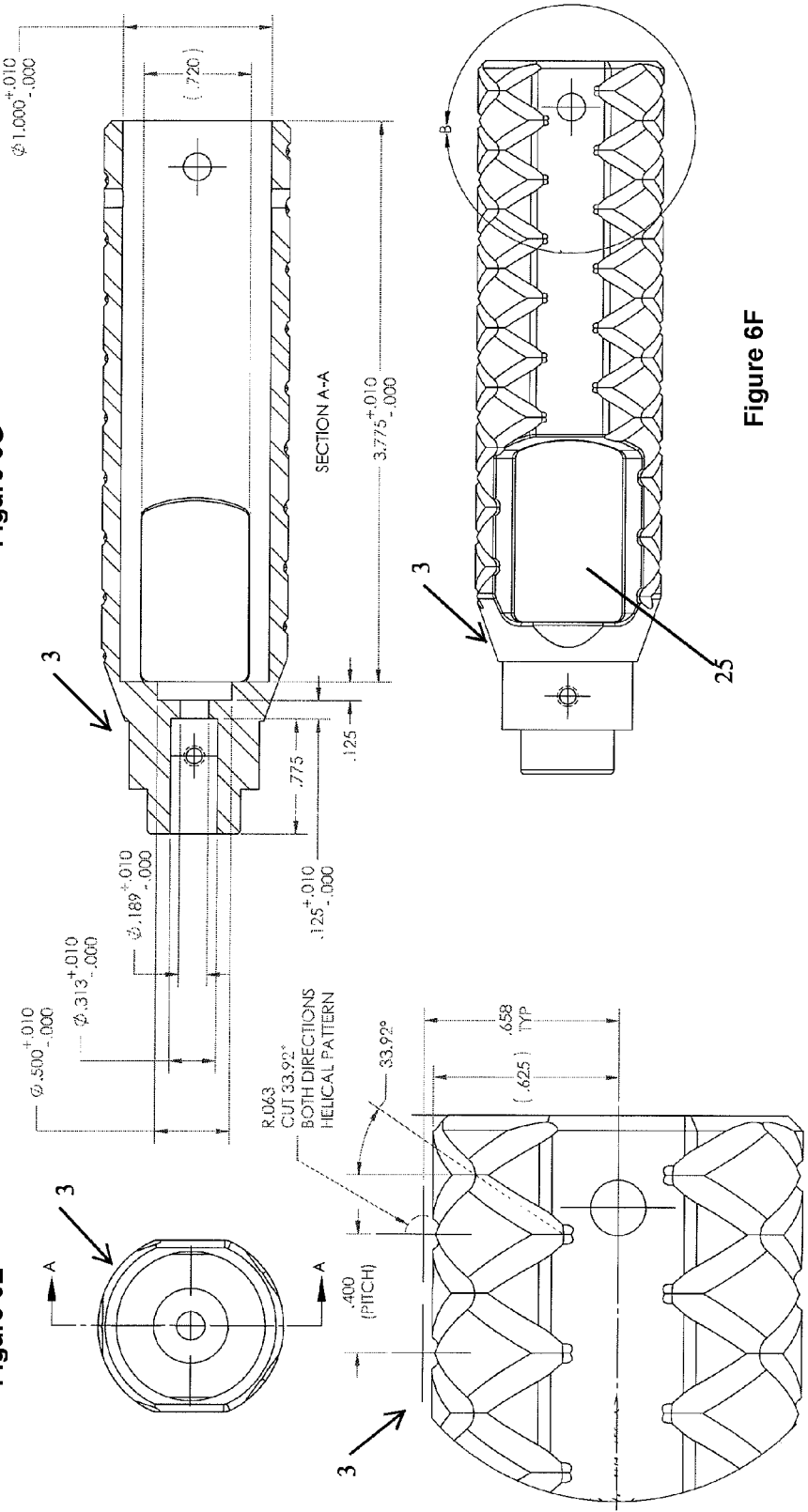

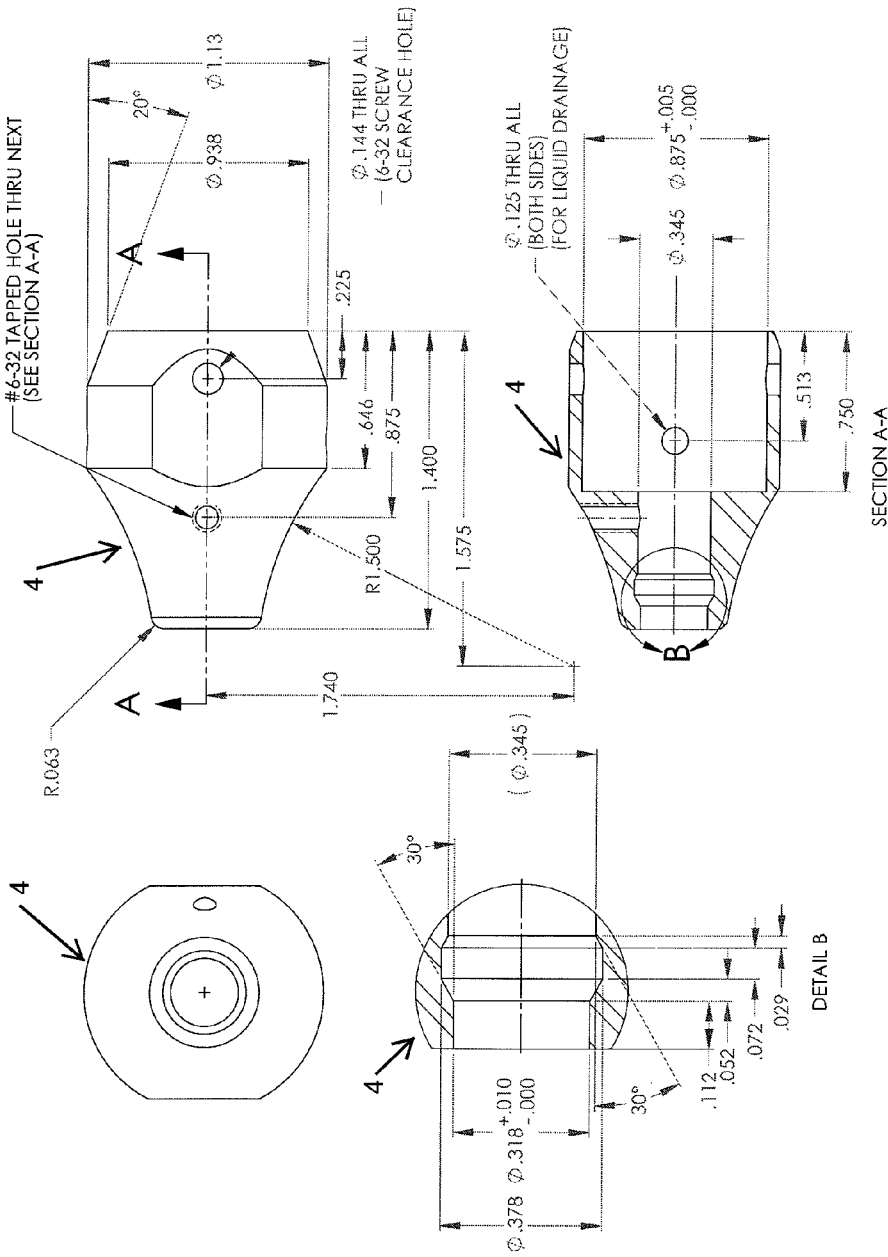

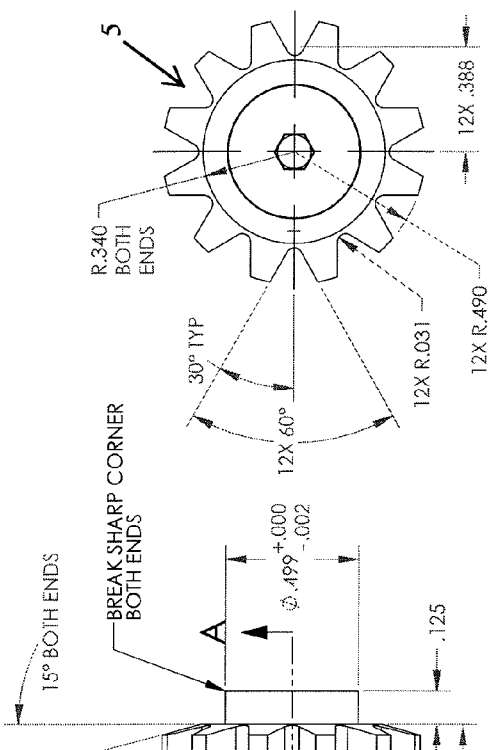
Figure 8C
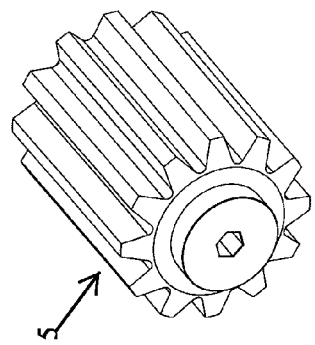
Figure 8E
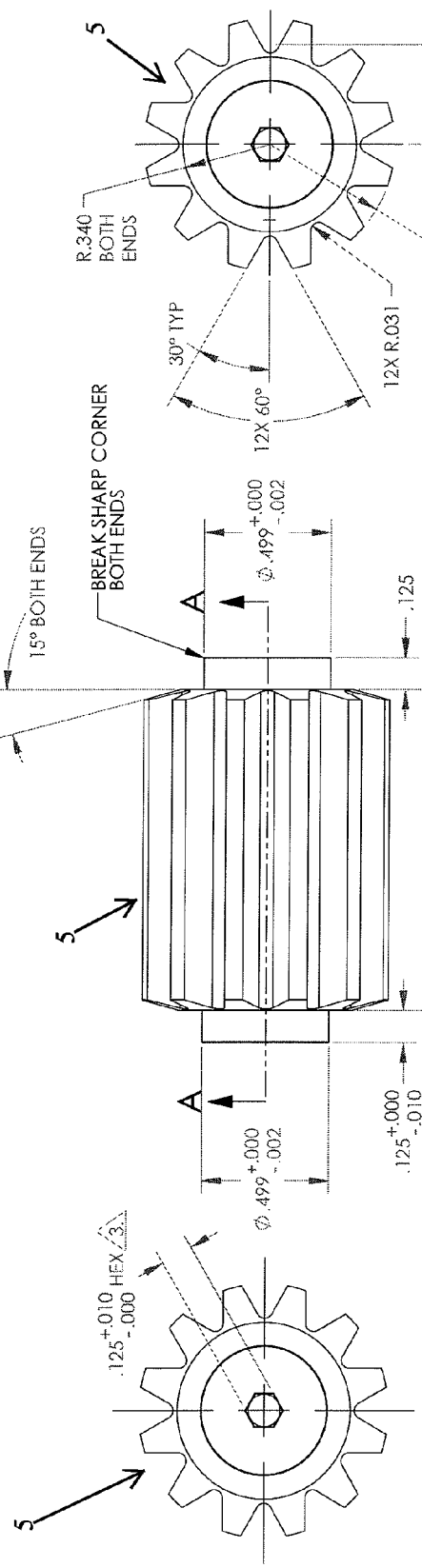
Figure 8B
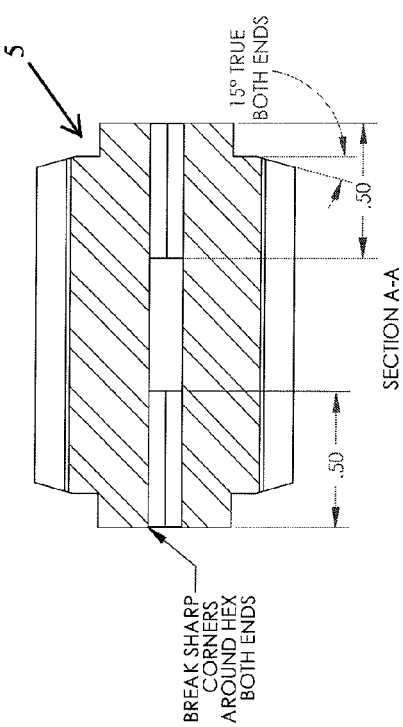
Figure 8D
Figure 8A

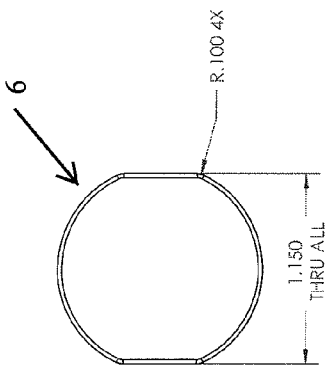
Figure 9B
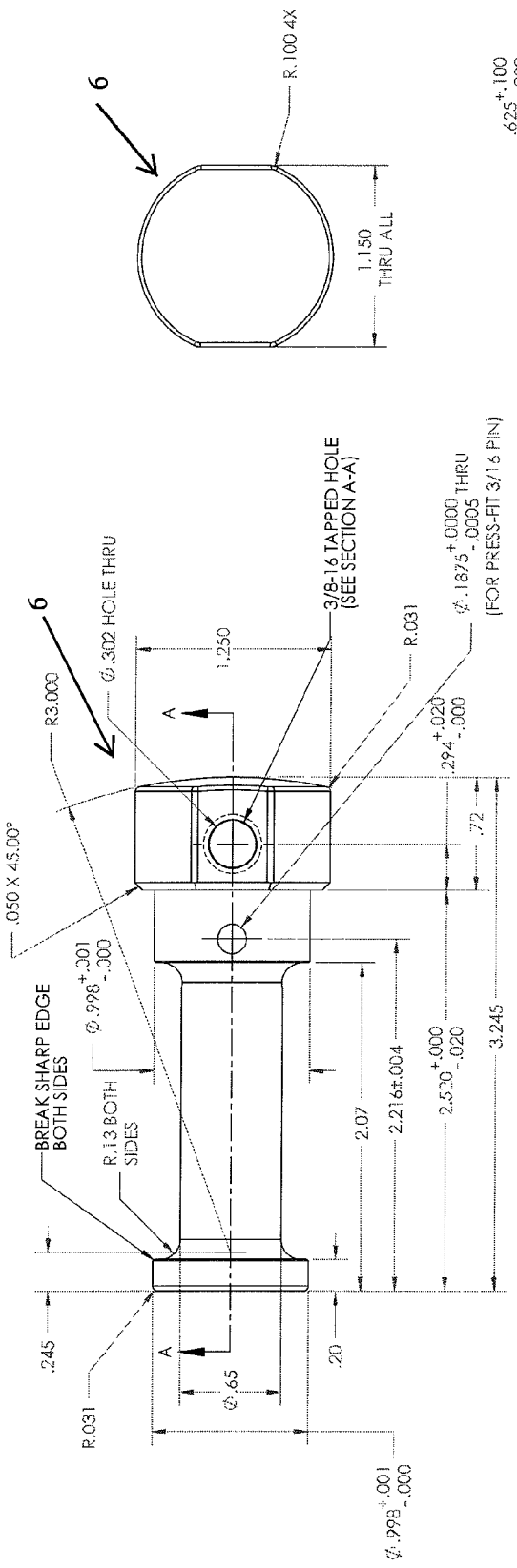
Figure 9A
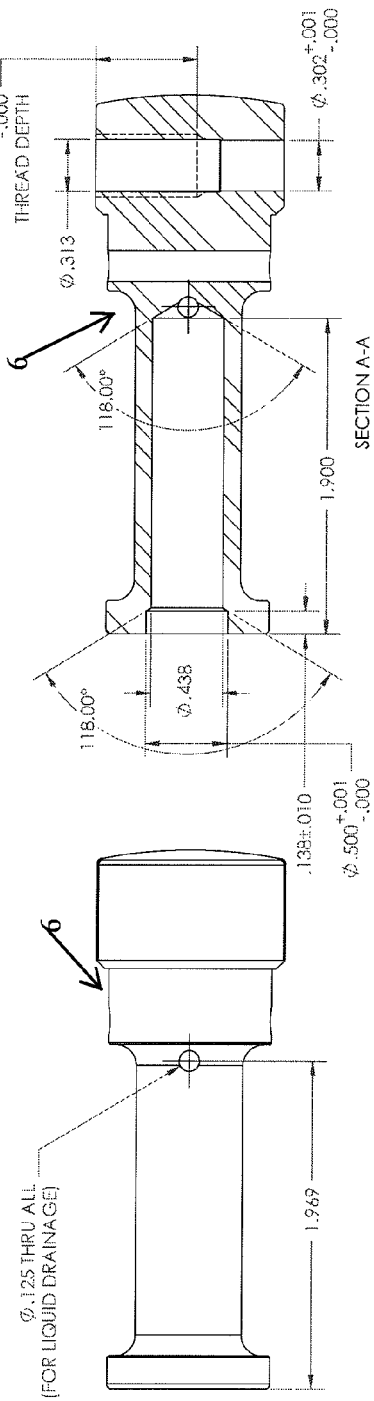
Figure 9D
Figure 9C

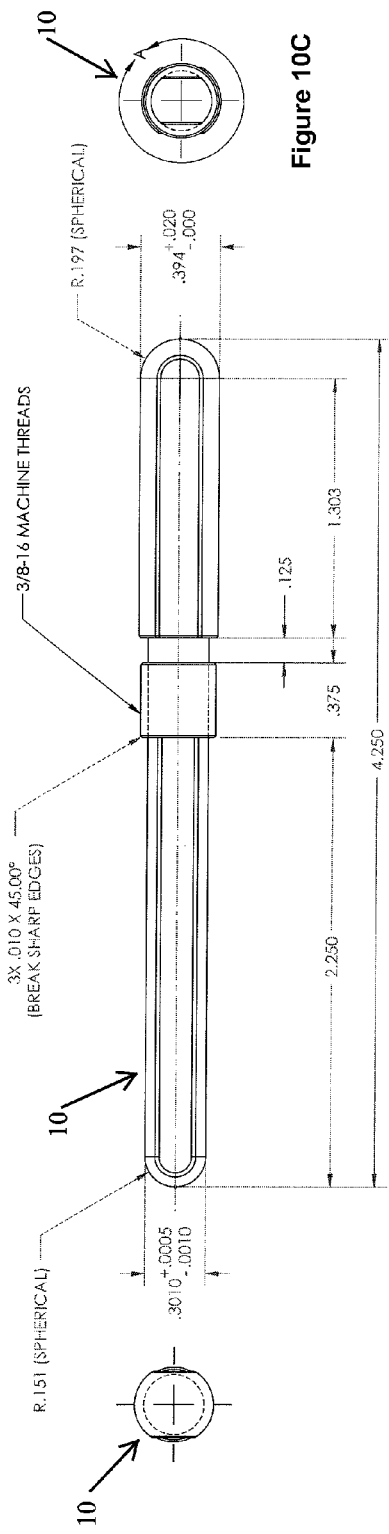
Figure 10A
Figure 10B
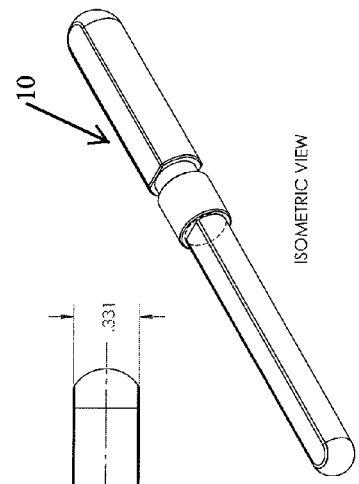
Figure 10C
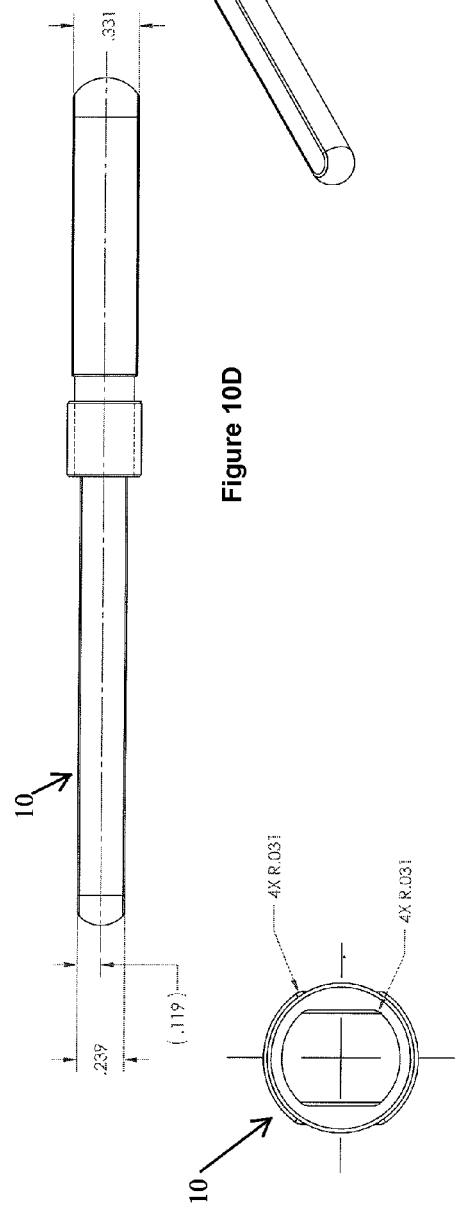
Figure 10D
Figure 10E
Figure 10F

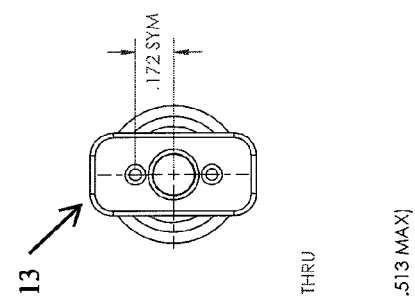
Figure 12B
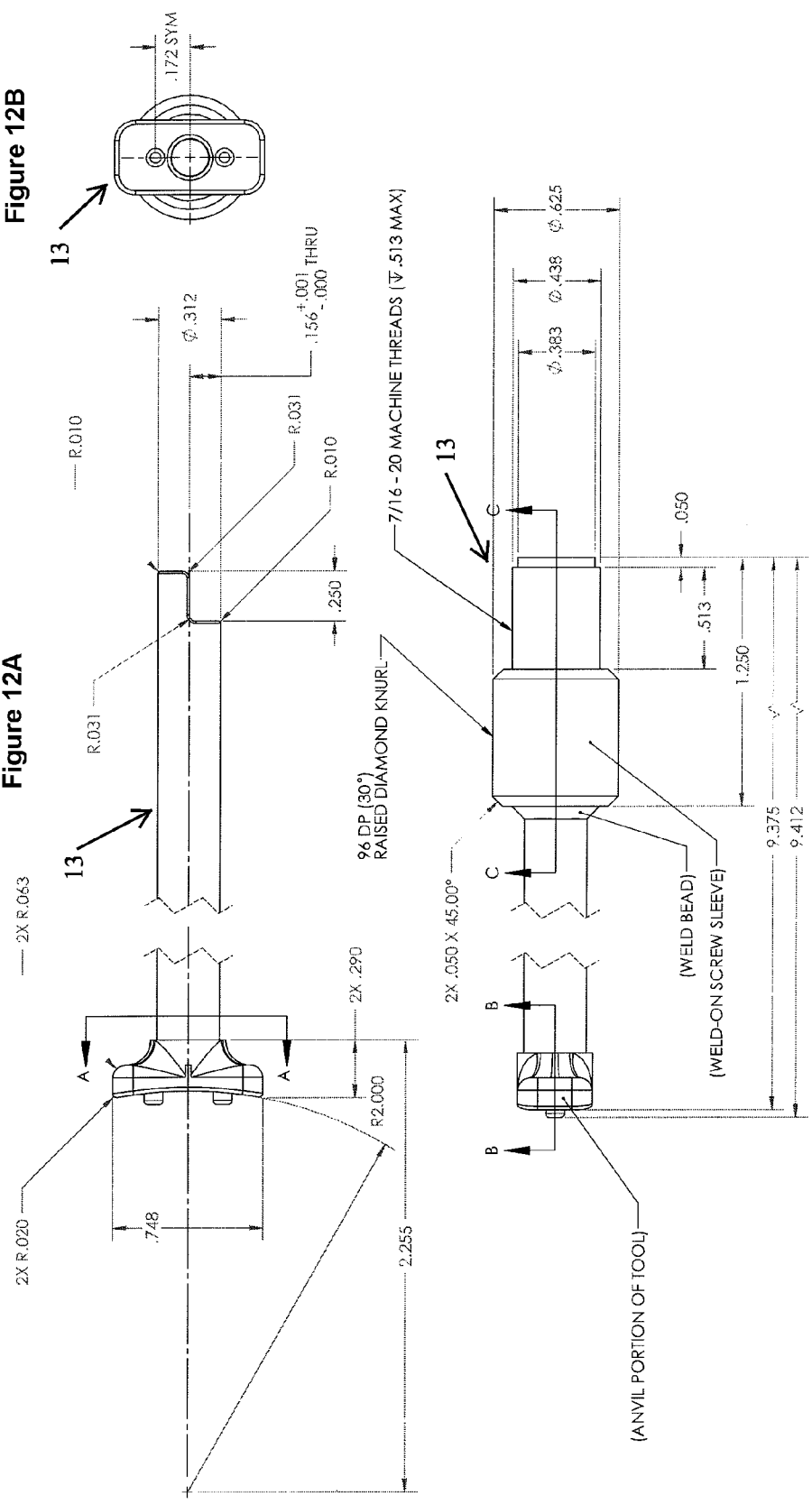
Figure 12A
Figure 12C

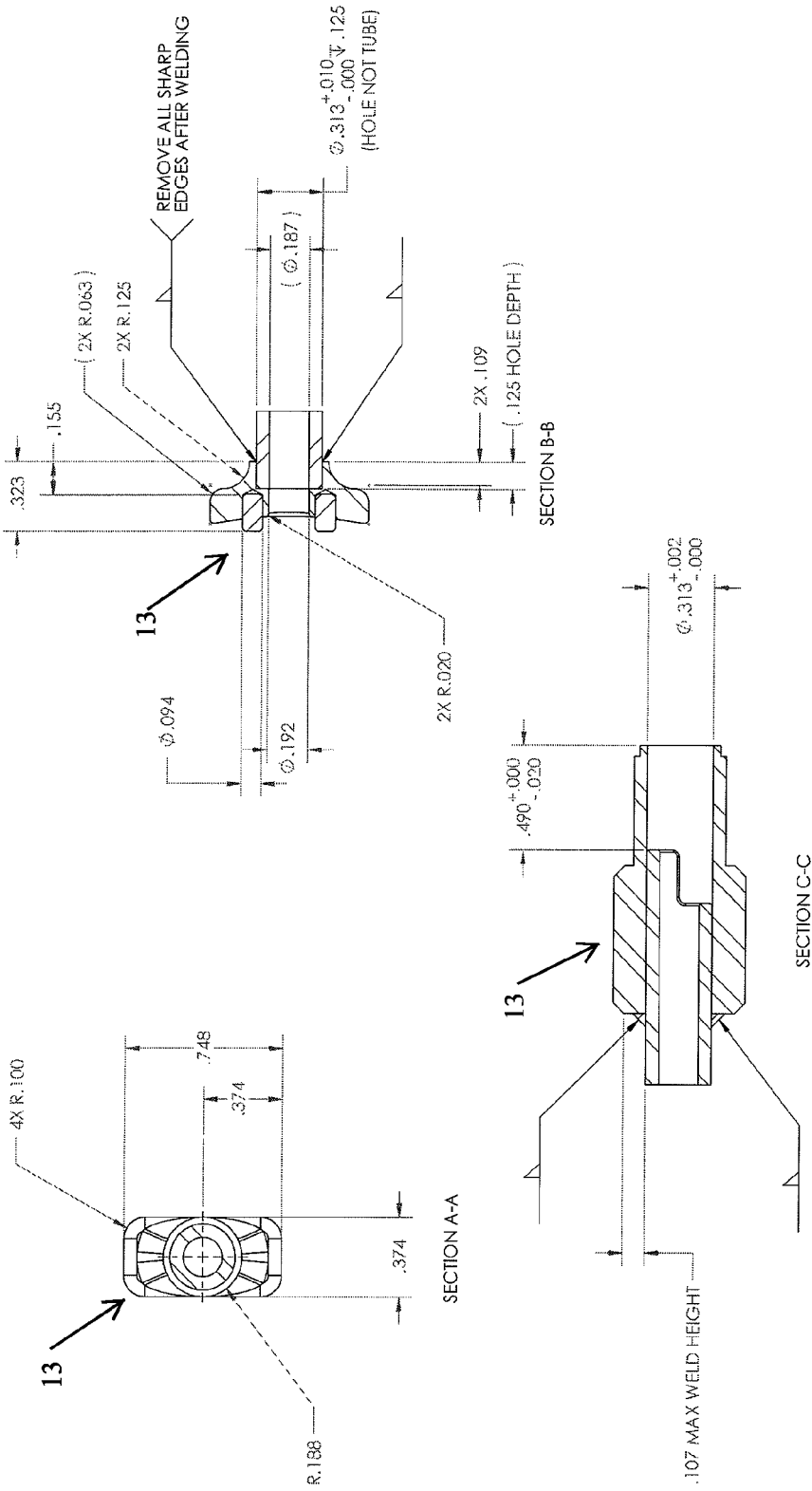

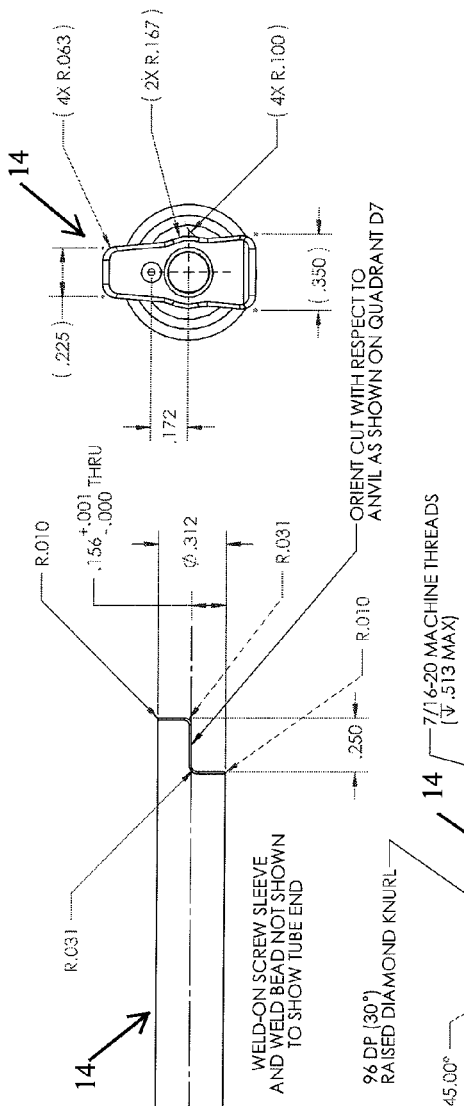
Figure 13A
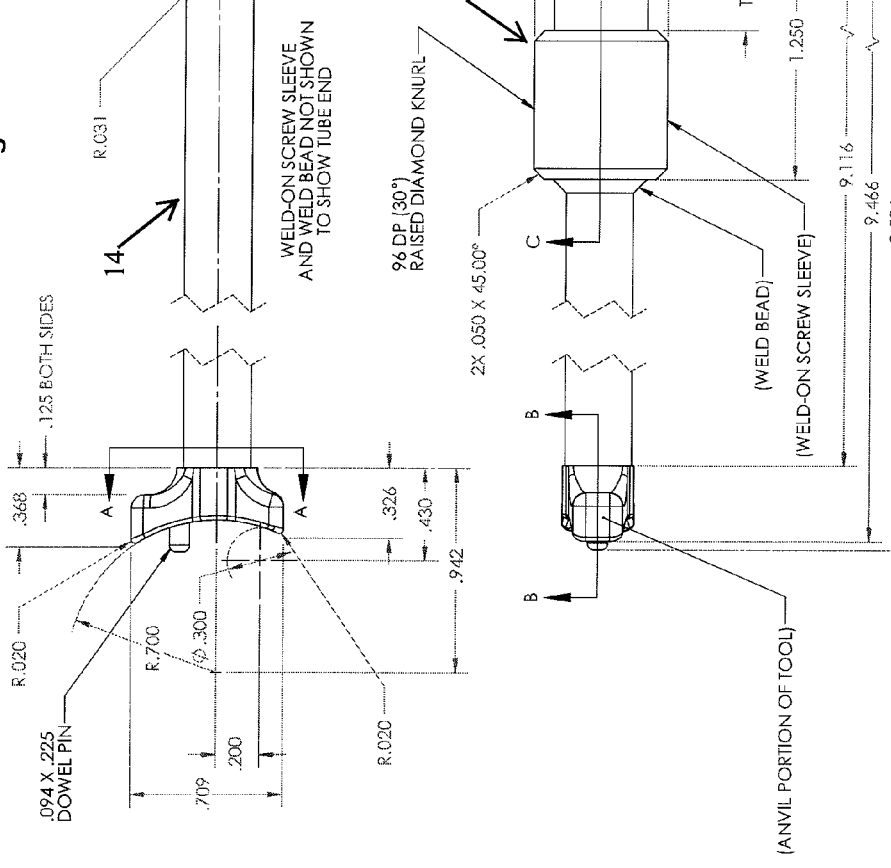
Figure 13B
Figure 13C

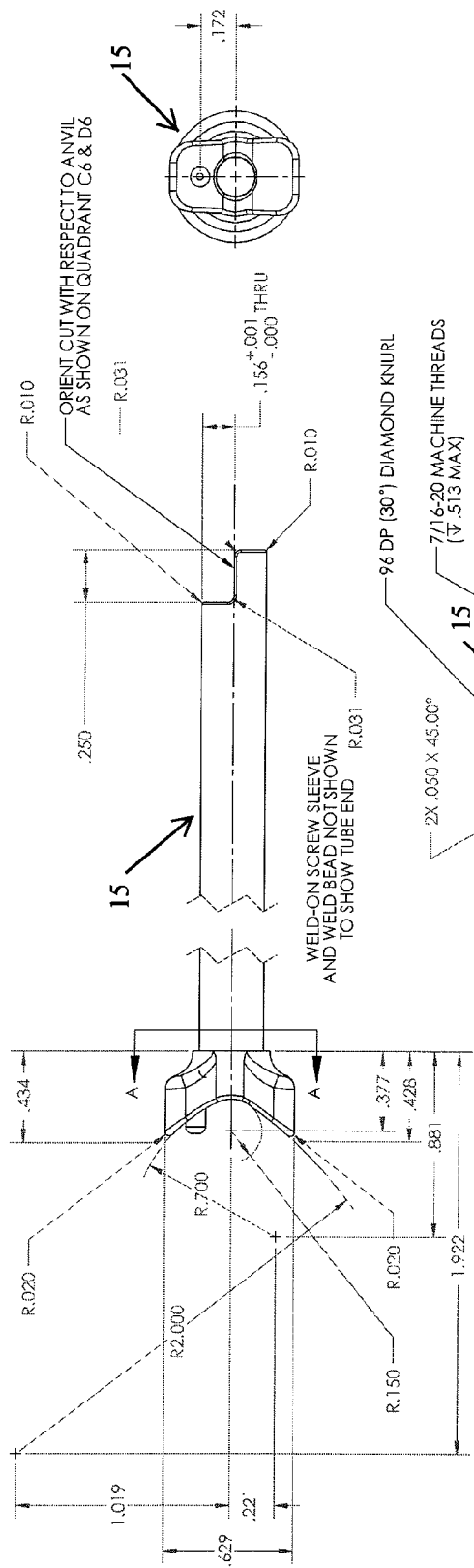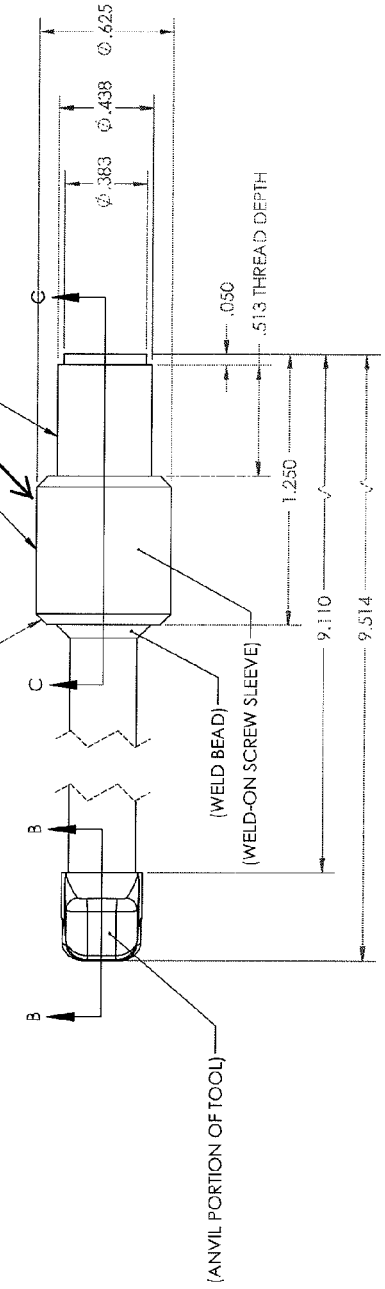

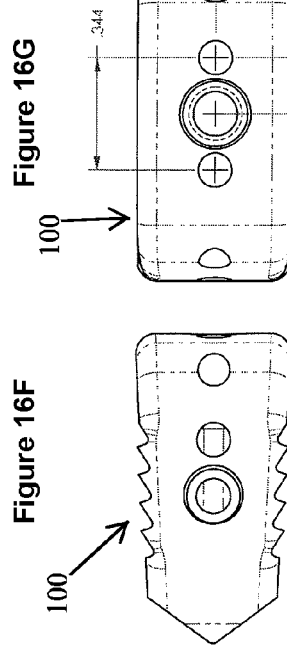
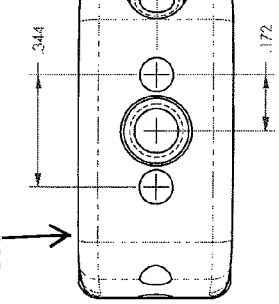
Figure 16F Figure 16G Figure 16H Figure 16I Figure 16J Figure 16K Figure 16L

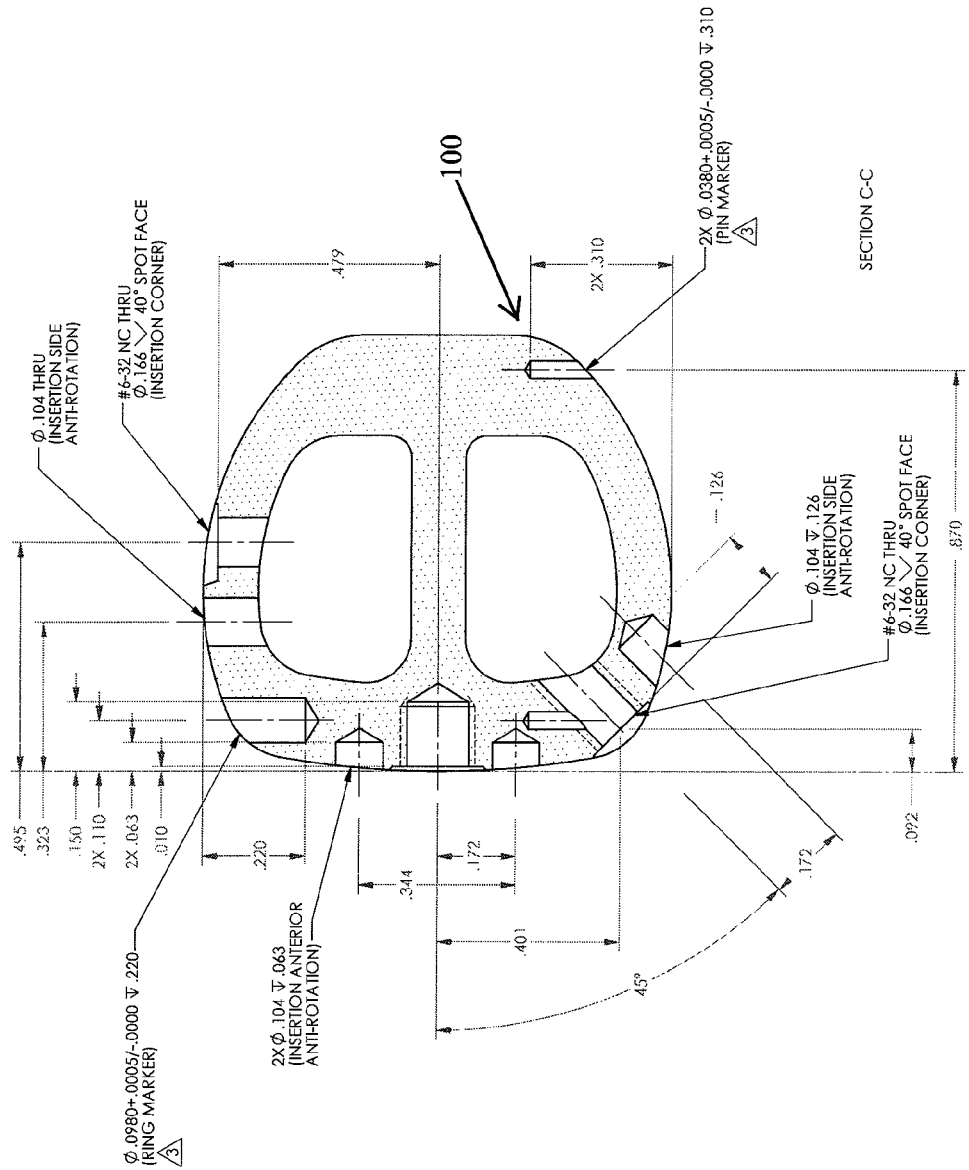
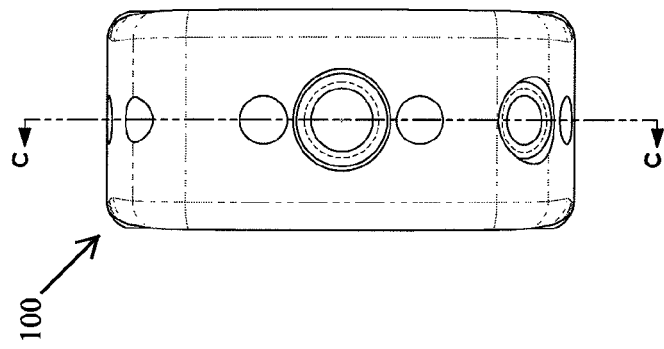

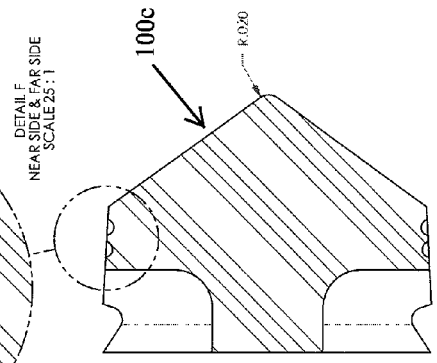
Figure 19D
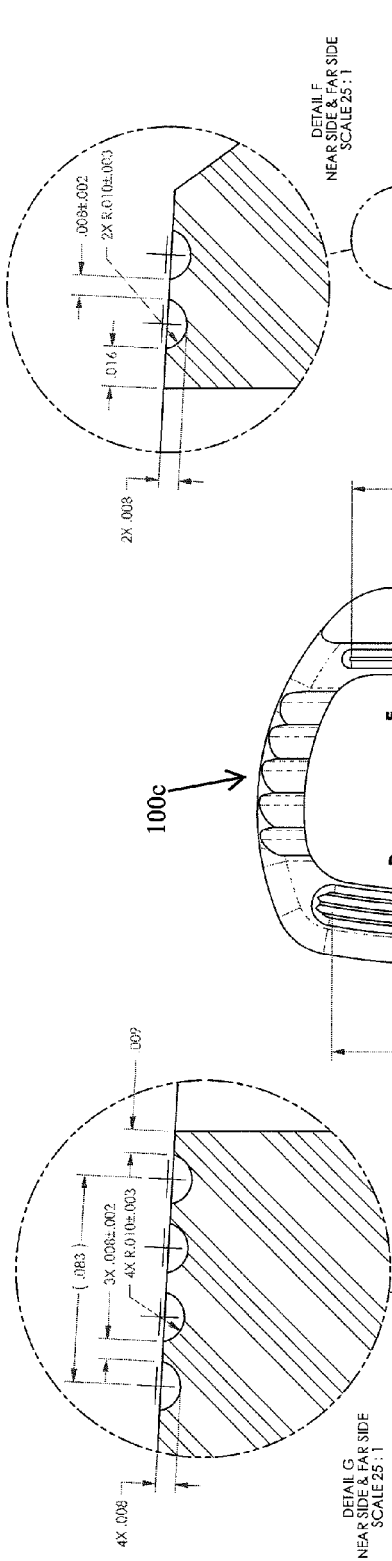
Figure 19E
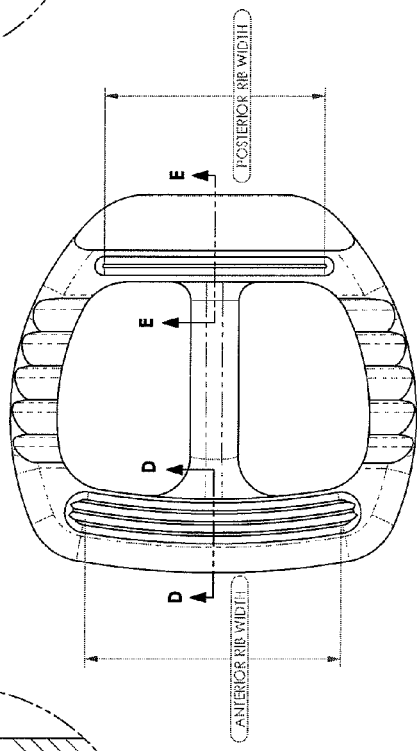
Figure 19A
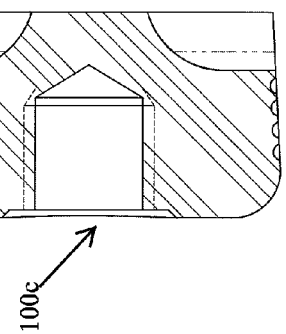
Figure 19B
Figure 19C

INTERBODY INSERTION TOOL AND METHOD

CROSS-REFERENCE TO RELATED APPLICATION

The present application claims priority under 35 U.S.C. §119(e) to U.S. Provisional Application Patent Application No. 61/745,922, filed on Dec. 26, 2012, which is hereby incorporated by reference in its entirety.

BACKGROUND

Field

The field of the invention relates to spinal surgery, and more particularly to methods, systems, and devices for spinal surgical procedures involving interbody fusions.

Description of the Related Art

Spinal surgery may be used to alleviate back pain and correct spinal disorders due to various causes including spinal disease, abnormalities, or trauma. Surgeons use spinal fusion during some forms of spinal surgery to join two or more vertebrae of a patient's spine. The procedure may include supplementary bone tissue in conjunction with the body's natural bone growth processes to fuse the vertebrae. Additionally, an interbody fusion cage (or spine cage) may be used in spinal fusion to maintain foraminal height and decompression. By fusing and/or aligning the spinal vertebrae, surgeons can reduce back pain and promote healing in the patient.

Surgeons often encounter difficulty in the surgical procedures for installing spine cages. Disadvantages associated with prior art reduction methods and devices include complicated procedures and patient trauma. Thus, methods, systems, and devices for improved interbody fusion are desired.

SUMMARY OF CERTAIN EMBODIMENTS

The present application relates to a tool used during spinal surgical procedures involving interbody fusions. Such procedures may include, but are not limited to, anterior lumbar interbody fusion (ALIF), oblique lumbar interbody fusion (OLIF), direct lateral interbody fusion (sometimes referred to as an XLIF or DLIF), posterior lumbar interbody fusion (PLIF) and transverse lumbar interbody fusion (TLIF). These procedures may also involve cervical interbody procedures most commonly in, but not limited to, anterior cervical discectomy fusion surgery (ACDF). During the procedure, a surgeon inserts and secures an interbody device into a void inside of the vertebra, which could be an implant sometimes called a vertebral replacement device (VBR) or between adjacent vertebra in the disc space which could be an implant commonly called a cage, so as to restrict motion in that vertebral segment of the spine. For simplicity, all devices used in the previously mentioned procedures, will be referred to as a "cage" herein. Disclosed herein is a novel tool and cage design for use during an interbody spinal fusion procedure. One embodiment of the tool described herein comprises a rod centrally located within the tool that has the ability to remain attached to the cage to aid in: coupling the tool to the cage, release of the tool from the cage, alignment of additional hardware, and insertion of materials within the hollow of the cage.

BRIEF DESCRIPTION OF THE DRAWINGS

FIG. 3A is an elevational view of another embodiment of an interbody insertion tool engaged with a spinal cage.

FIG. 3B is a cross sectional view of the tool and spinal cage taken along line A-A of FIG. 3A.

FIGS. 4A-4C are elevational views of a fixed tube welded component illustrated in FIG. 1. FIG. 4D is a cross-sectional view of the component taken along line A-A of FIG. 4C.

FIGS. 5A and 5B are elevational views of an anterior inner rod component illustrated in FIG. 1.

FIGS. 6A-6D are elevational views of a main body component illustrated in FIG. 1.

FIGS. 6E and 6F are elevational views of the main body component illustrated in FIG. 1. FIG. 6G is a cross-sectional view of the main body component taken along line A-A of FIG. 6E. FIG. 6H is a detail view of section B of FIG. 6F.

FIGS. 7A-7C are elevational views of a locking head component illustrated in FIG. 1. FIG. 7D is a cross-sectional view of the locking head component taken along line A-A of FIG. 7B. FIG. 7E is a detail view of section B of FIG. 7D. FIG. 7F is a perspective view of the locking head component illustrated in FIG. 1.

FIGS. 8A-8C are elevational views of a thumb roller component illustrated in FIG. 1. FIG. 8D is a cross-sectional view of the thumb roller component taken along line A-A of FIG. 8B. FIG. 8E is a perspective view of the thumb roller component illustrated in FIG. 1.

FIGS. 9A-9C are elevational views of an inner plug component illustrated in FIG. 1. FIG. 9D is a cross-sectional view of the inner plug component taken along line A-A of FIG. 9A.

FIGS. 10A-10D are elevational views of a threaded T-handle component illustrated in FIG. 1. FIG. 10E is a detail view of section A of FIG. 10C. FIG. 10F is a perspective view of the threaded T-handle component illustrated in FIG. 1.

FIGS. 12A-12C are elevational views of an anterior insertion tool component illustrated in FIG. 1. FIG. 12D is a cross-sectional view of the anterior insertion tool component taken along line A-A of FIG. 12A. FIG. 12E is a cross-sectional view of the anterior insertion tool component taken along line B-B of FIG. 12B. FIG. 12F is a cross-sectional view of the anterior insertion tool component taken along line C-C of FIG. 12C.

FIGS. 13A-13C are elevational views of a lateral insertion tool component illustrated in FIG. 1.

FIGS. 14A-14C are elevational views of an oblique insertion tool component illustrated in FIG. 1.

FIGS. 16F-16J are elevational views of the cage assembly of FIG. 16A. FIG. 16K is a cross-sectional view of the cage assembly taken along line A-A of FIG. 16J. FIG. 16L is a detail view of section B of FIG. 16H.

FIG. 17A is an elevational view of another embodiment of a spinal cage assembly for use with the interbody insertion tool of FIG. 1. FIG. 17B is a cross-sectional view taken along line C-C of FIG. 17A.

FIG. 19A is an elevational view of still another embodiment of a spinal cage assembly for use with the interbody insertion tool of FIG. 1. FIG. 19B is a cross-sectional view taken along line D-D of FIG. 19A. FIG. 19C is a detail view of section G of FIG. 19B. FIG. 19D is a cross-sectional view taken along line E-E of FIG. 19A. FIG. 19E is a detail view of section F of FIG. 19D.

DETAILED DESCRIPTION

Any feature or combination of features described herein are included within the scope of the present invention provided that the features included in any such combination are not mutually inconsistent as will be apparent from the context, this description, and the knowledge of one skilled in the art. In addition, any feature or combination of features may be specifically excluded from any embodiment of the present invention. For purposes of summarizing the present invention, certain aspects, advantages, and novel features of the present invention are described herein. Of course, it is to be understood that not necessarily all such aspects, advantages, or features will be present in any particular embodiment of the present invention.

In reference to the disclosure herein, for purposes of convenience and clarity only, directional terms, such as top, bottom, left, right, up, down, upper, lower, over, above, below, beneath, rear, and front may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

Tool and Cage System

Figure 1:
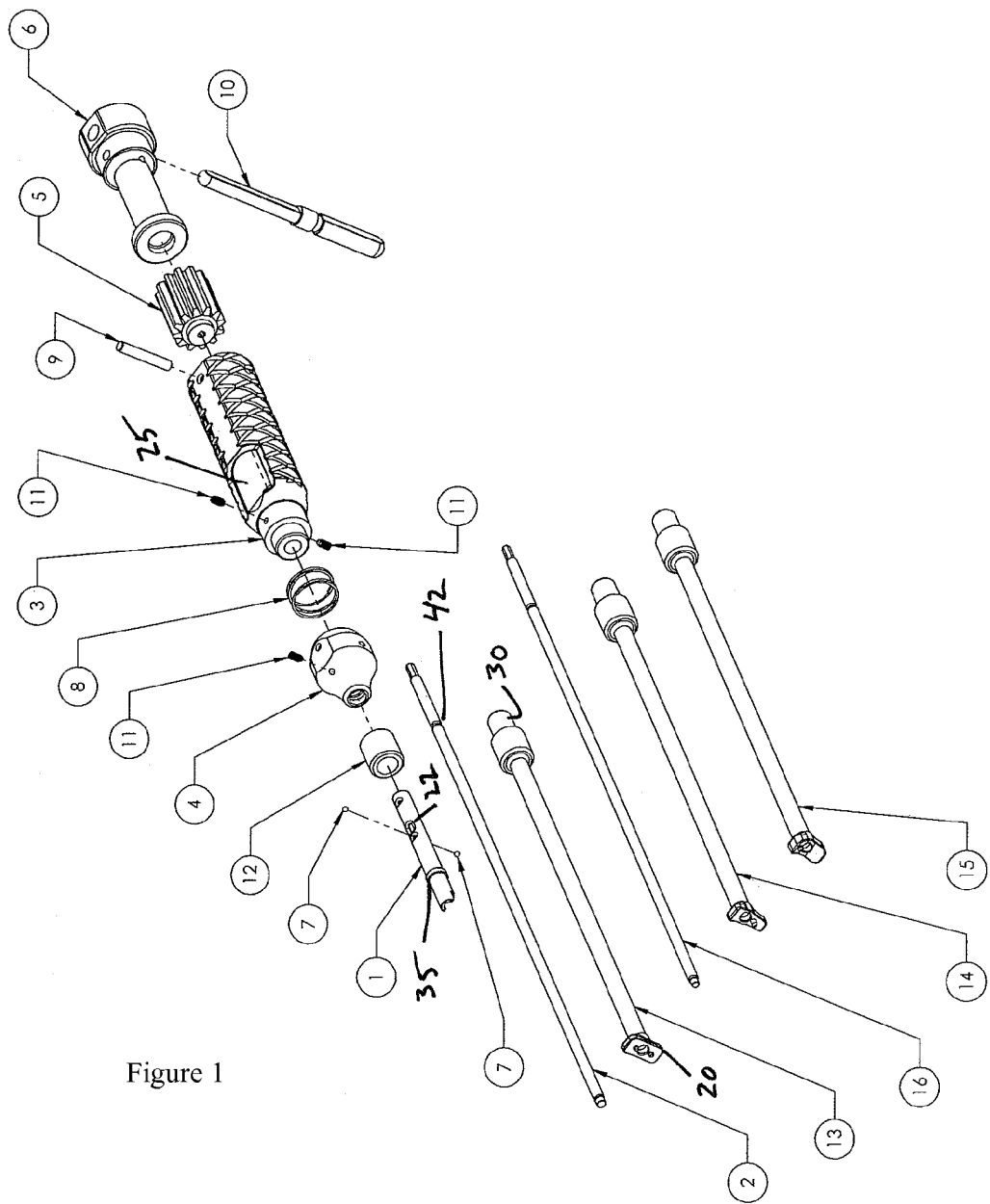
FIG. 1 is an exploded perspective view of one embodiment of an interbody insertion tool.

Disclosed herein is a novel tool and cage design for use during an interbody spinal fusion procedure. FIG. 1 illustrates an exploded view of an exemplary embodiment of the tool. FIG. 3A illustrates the tool of FIG. 1 in an assembled condition, and FIG. 3B illustrates a cross section. The tool includes a cage attachment portion, a coupling portion, and a handle portion. The cage attachment portion of the tool is selected based upon the surgery to be performed (e.g., ALIF, OLIF, PLIF, TLIF, cervical interbody or any other procedure that involves an implant placed inside the disc space or vertebral body). The fully assembled tool, such as the embodiment illustrated in FIG. 3A, has both a proximal and a distal end, the proximal end being located on the handle portion and the distal end being located on the cage attachment portion. Items 3, 5, 6, 9, and 10 comprise the handle portion of the tool, items 1, 4, 7, 8, and 12 comprise the coupling portion of the tool, and items 2 and 13-16 selectively comprise the cage attachment portion of the tool.

During a spinal fusion operation, the surgeon may use the tool to insert a cage between vertebral bodies. The cage attachment portion of the tool is such that the cage securely couples to the tool to distribute the insertion force across the body of the cage. After the surgeon has inserted the cage into the spinal column, the surgeon may remove most of the tool from the cage by manipulating the coupling portion of the tool. When the most of the tool is removed in this manner, a rod from the cage attachment portion (e.g., inner rod 2 or 16) slides out of the tool, remaining engaged to the cage. With the rod remaining engaged to the cage, the surgeon is able to use it as an alignment reference for additional hardware used later in the procedure to secure the cage in place. Further, the rod may be cannulated to provide a fluidic connection between the proximal end of the rod and the interior of the cage. This allows the surgeon to inject a biologic or other therapeutic material directly into the operative site to improve patient healing and post-operative recovery. Thus, use of the tool has several benefits, including, but not limited to, secure coupling of the tool to the cage, the quick-release of the tool from the cage, the ability to precisely align additional hardware using the inner rod, and the ability to insert materials directly within the hollow of the cage.

Referring simultaneously to FIGS. 1 and 3B, the cage attachment portion of the tool may alternatively include an anterior inner rod 2 with an anterior insertion tool 13 or an oblique and lateral inner rod 16 with either a lateral insertion tool 14 or an oblique insertion tool 15 (depending on the surgical procedure to be performed). Assuming an ALIF procedure, a proximal end of anterior inner rod 2 is inserted through a fixed tube 1. A locking head 4 on the coupling portion of the tool is moved into the coupling position to allow anterior inner rod 2 to pass through the coupling portion of the tool and engage a thumb roller 5 in the handle portion of the tool. A slot 42 on an outer surface of the anterior inner rod 2 aligns with an interface 50 (between the locking head 4 and the fixed tube 1) where locking balls 7 are present. With the anterior inner rod 2 engaged to the thumb roller 5, the locking head 4 may be released. A spring 8 moves the locking head 4 into a locked position in which locking balls 7 protrude from the inner surface of the fixed tube 1, engage the slot 42 and lock the anterior inner rod 2 to the handle portion and coupling portion of the tool. As mentioned, anterior inner rod 2 may be cannulated to provide a fluidic connection to the interior of a cage 100. Anterior insertion tool 13 may then be slid over anterior inner rod 2, a proximal end of the anterior insertion tool 13 engaging the keyed distal end of the fixed tube 1. The anterior insertion tool 13 includes a threaded outer surface 30 near its proximal end to secure via knurled nut 12.

Distal ends of the anterior inner rod 2 and the anterior insertion tool 13 are formed to engage the cage 100 used in the spinal fusion. An anvil 20, located on the distal end of anterior insertion tool 13, distributes forces applied to the cage and stabilizes the cage-tool interface. The distal end of anterior insertion tool 13 includes an alignment reference 21 to align the cage 100 to the tool and to prevent rotation. An outer surface of the distal end of the anterior inner rod 2 is threaded so as to engage a threaded inner surface of the cage. In the fully assembled tool, the thumb roller 5 allows the surgeon to screw on and unscrew the cage from the tool.

The handle portion of the tool includes a main body 3, a thumb roller 5, an inner plug 6, and a threaded t-handle 10, held together by a dowel pin 9. The main body 3 has a proximal and distal end, and an inner and outer surface. The main body 3 may be cylindrical in shape, with an inner surface cavity to allow coaxial insertion of the thumb roller 5 and the inner plug 6. The thumb roller 5 and the inner plug 6 are inserted at the proximal end of the main body 3. A distal end of the thumb roller 5 includes a cavity to engage the anterior inner rod 2. To secure the thumb roller 5 within the main body 3, the inner plug 6 is inserted and secured via the dowel pin 9. The main body 3 further includes at least one opening 25 to allow the surgeon to manipulate the housed thumb roller 5.

The main body 3 also includes holes for both liquid drainage and other hardware (e.g., dogpoint set screw 11, dowel pin 9, or threaded t-handle 10). The outer surface of the main body 3 may be formed so as to improve the surgeon's grip. The inner plug 6 may include a transaxial threaded hole that aligns with a hole in the main body 3 to allow insertion of the threaded t-handle 10. The threaded t-handle 10 shown here is cylindrical in shape, having rounded ends and a threaded segment along a portion of its length to engage the threaded hole of inner plug 6.

The coupling portion of the tool is located between the cage attachment portion and the handle portion. The coupling portion includes the fixed tube 1, the locking head 4, locking balls 7, the spring 8, and the knurled nut 12. The fixed tube 1 includes a proximal end and a distal end, and an inner and outer surface. The distal end of the fixed tube 1 is keyed to contact a portion of the cage attachment portion of the tool (e.g., anterior insertion tool 13, lateral insertion tool 14, or oblique insertion tool 15). The proximal end of the fixed tube 1 is inserted through the knurled nut 12, the locking head 4, and the spring 8 and then into the distal end of main body 3. Locking balls 7 are provided so as to be positioned at an interface 50 between the fixed tube 1 and the locking head 4. The fixed tube 1 is secured to the main body 3 via dogpoint set screws 11. A flange 35 on the fixed tube 1 secures the knurled nut 12 so that knurled nut 12 may rotate and slide along a distance of the fixed tube 1 but does not slide off distal end of fixed tube 1 due to shoulder 40 contact with flange 35. Knurled nut 12 includes an outer, knurled surface and an inner, threaded surface to secure insertion tool 13.

The fixed tube 1 further includes an alignment notch 22. Locking head 4 is rotatably secured and aligned to fixed tube 1 via a dogpoint set screw 11 engaged to the alignment notch 22. The alignment notch 22 allows the locking head 4 to slide between a first, locked position and a second, coupling position. The spring 8 is disposed between the locking head 4 and the main body 3 to force locking head 4 into the default locked position. In the locked position, an inner surface of the locking head 4 forces the locking balls 7 to protrude from the inner surface of the fixed tube 1 into the slot 42 on the inner rod 2. By sliding the locking head 4 against the force of the spring 8, a surgeon may move the locking head 4 into the coupling position. In the coupling position, a recess 60 within the inner surface of the locking head 4 allows the locking balls 7 to recede out of the slot 42.

Figure 2:
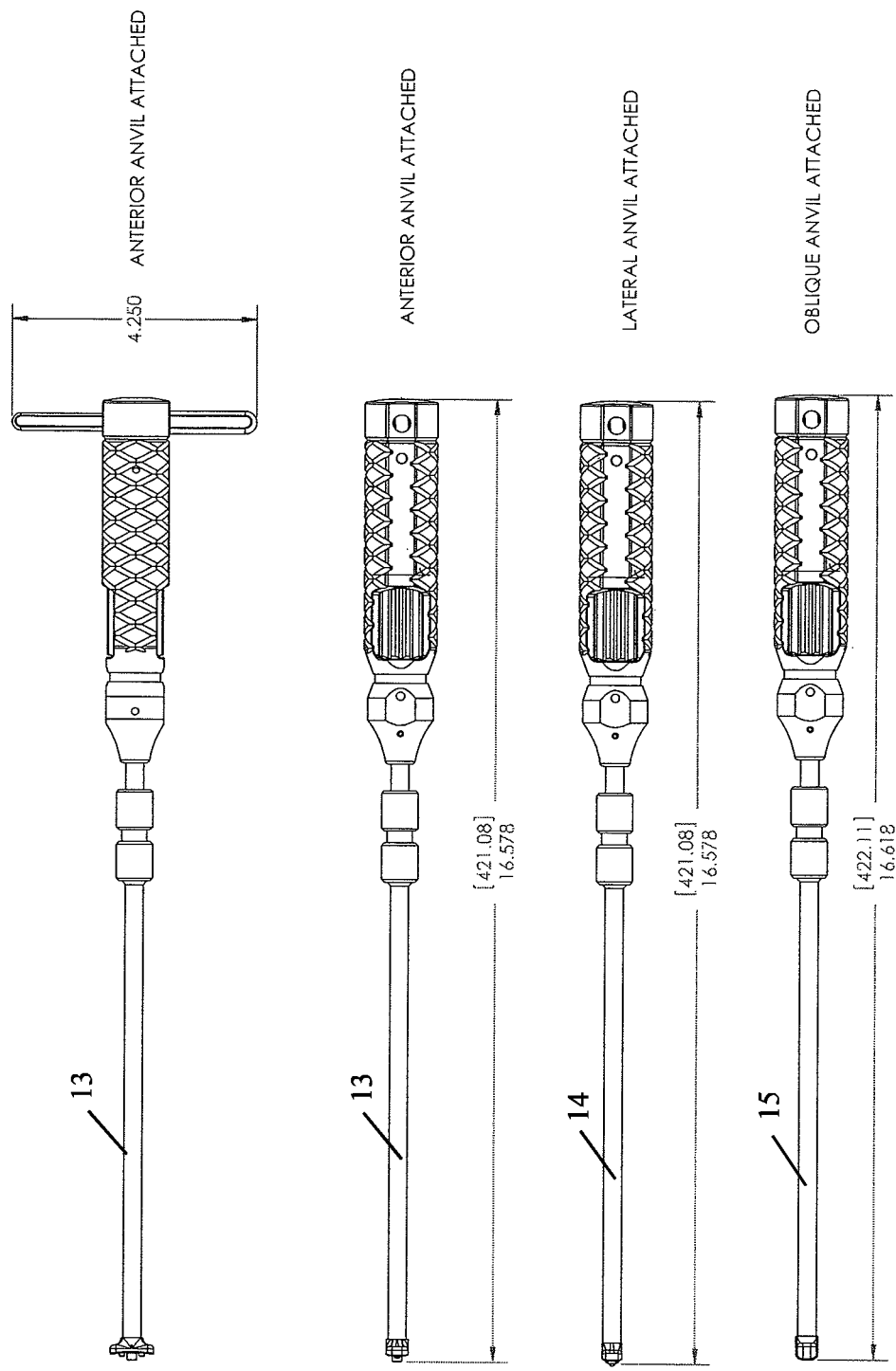
FIG. 2 illustrates the tool of FIG. 1 in various cage attachment portion configurations.

FIG. 2 illustrates the tool in various cage attachment portion configurations. Although not illustrated, the cage may include internal channels in fluid communication with the distal end of a cannulated rod 2 or 16 to guide and/or route any injected or implanted therapeutic or other substance to a desired location in or around the cage. These channels may lead into both the interior cavity of the cage and or to the exterior of the cage so that the fluid can be introduced inside the cage or to immediate area outside of the cage.

Figures 11A, 11B, 11C:
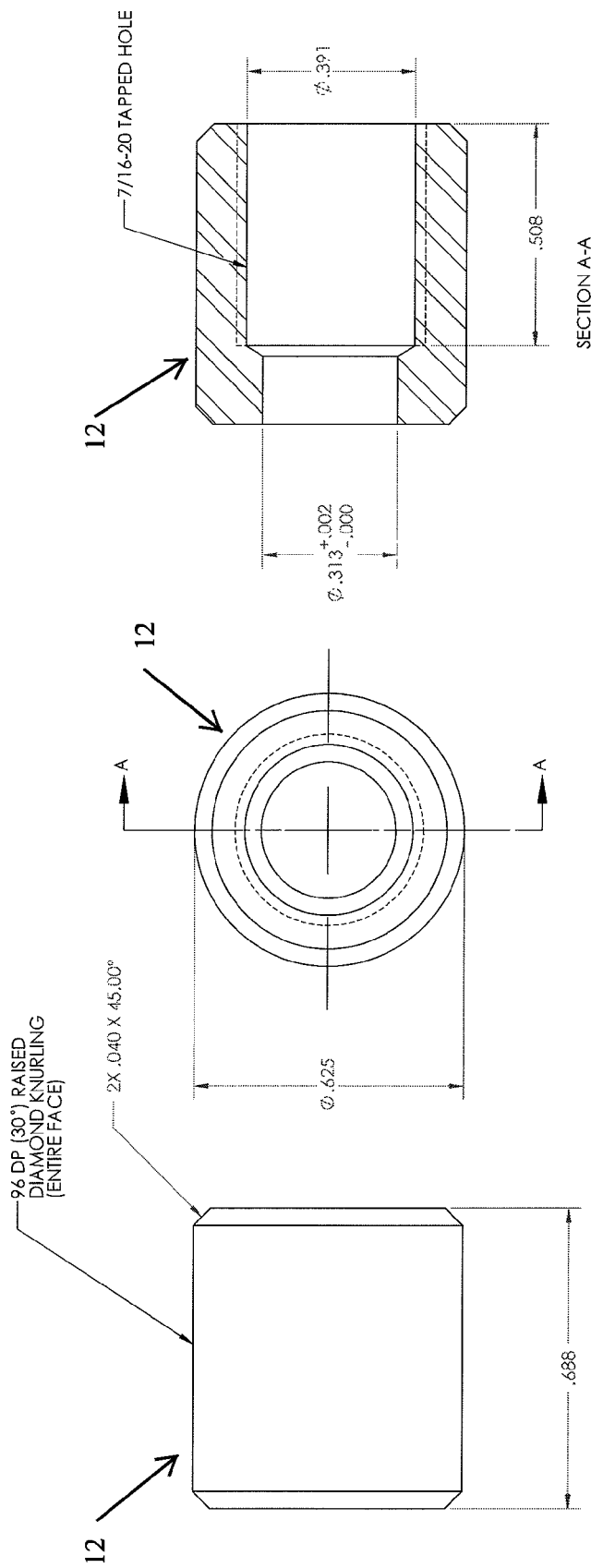
FIGS. 11A and 11B are elevational views of a knurled nut component illustrated in FIG. 1.
FIG. 11C is a cross-sectional view of the knurled nut component taken along line A-A of FIG. 11B.
Figures 13D, 13E, 13F:
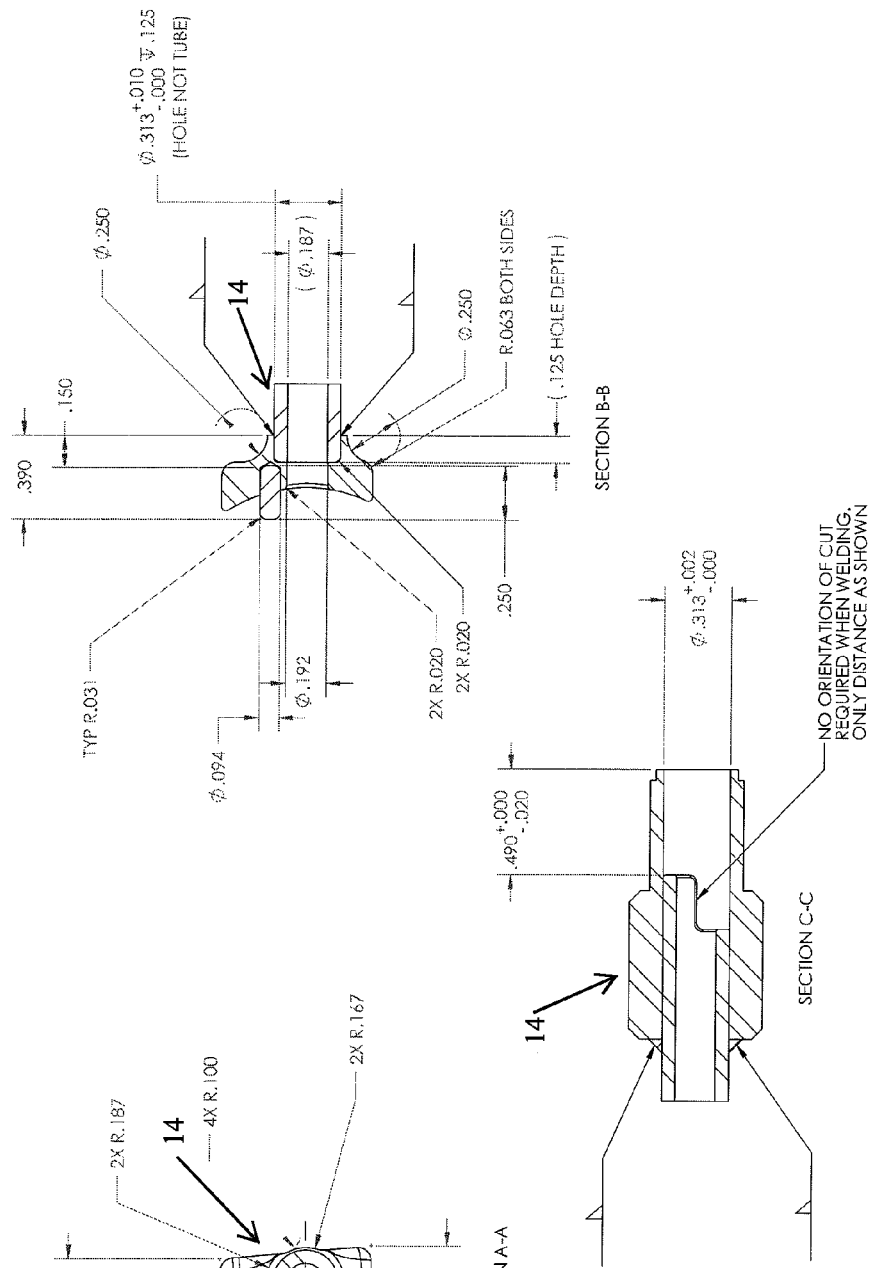
FIG. 13D is a cross-sectional view of the lateral insertion tool component taken along line A-A of FIG. 13A.
FIG. 13E is a cross-sectional view of the lateral insertion tool component taken along line B-B of FIG. 13B.
FIG. 13F is a cross-sectional view of the lateral insertion tool component taken along line C-C of FIG. 13C.
Figure 14E:
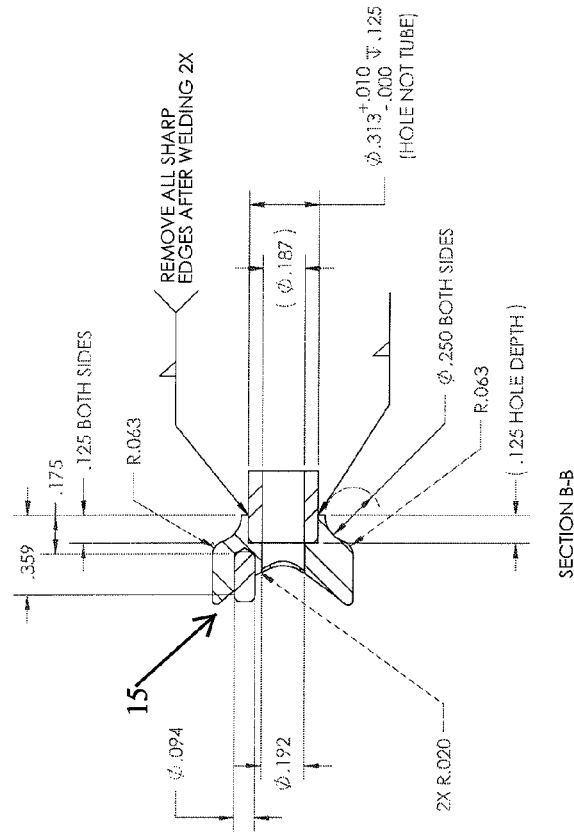
FIG. 14E is a cross-sectional view of the oblique insertion tool component taken along line B-B of FIG. 14B.
Figure 14D:
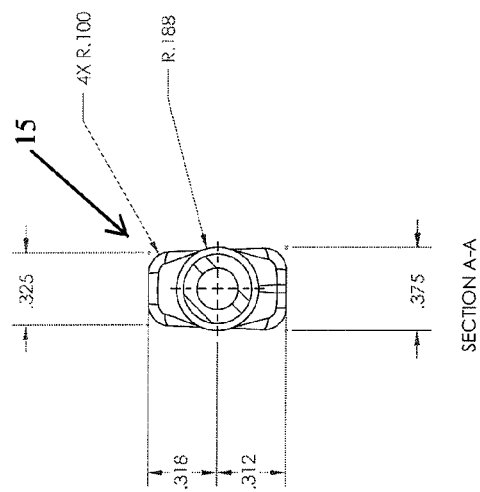
FIG. 14D is a cross-sectional view of the oblique insertion tool component taken along line A-A of FIG. 14A.
Figure 14F:
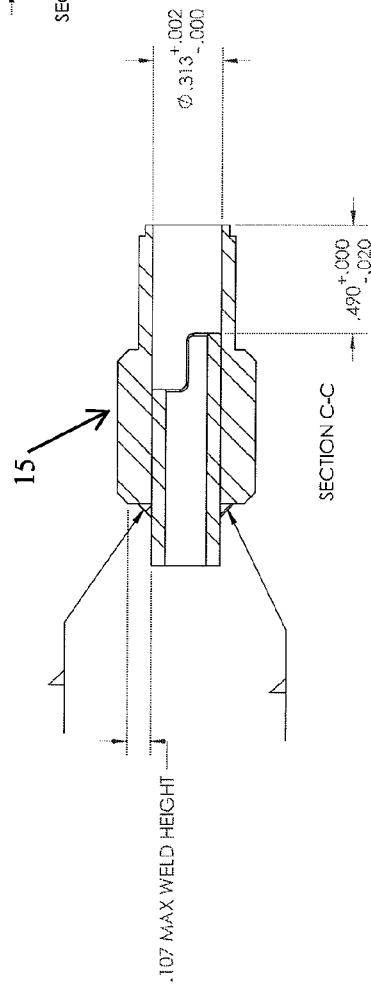
FIG. 14F is a cross-sectional view of the oblique insertion tool component taken along line C-C of FIG. 14C.
Figure 15B:
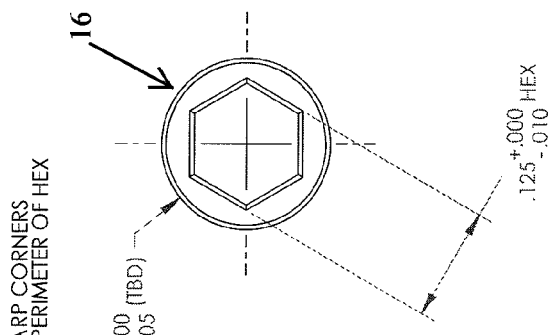
FIGS. 15A and 15B are elevational views of an oblique and lateral inner rod component illustrated in FIG. 1.
Figure 15A:
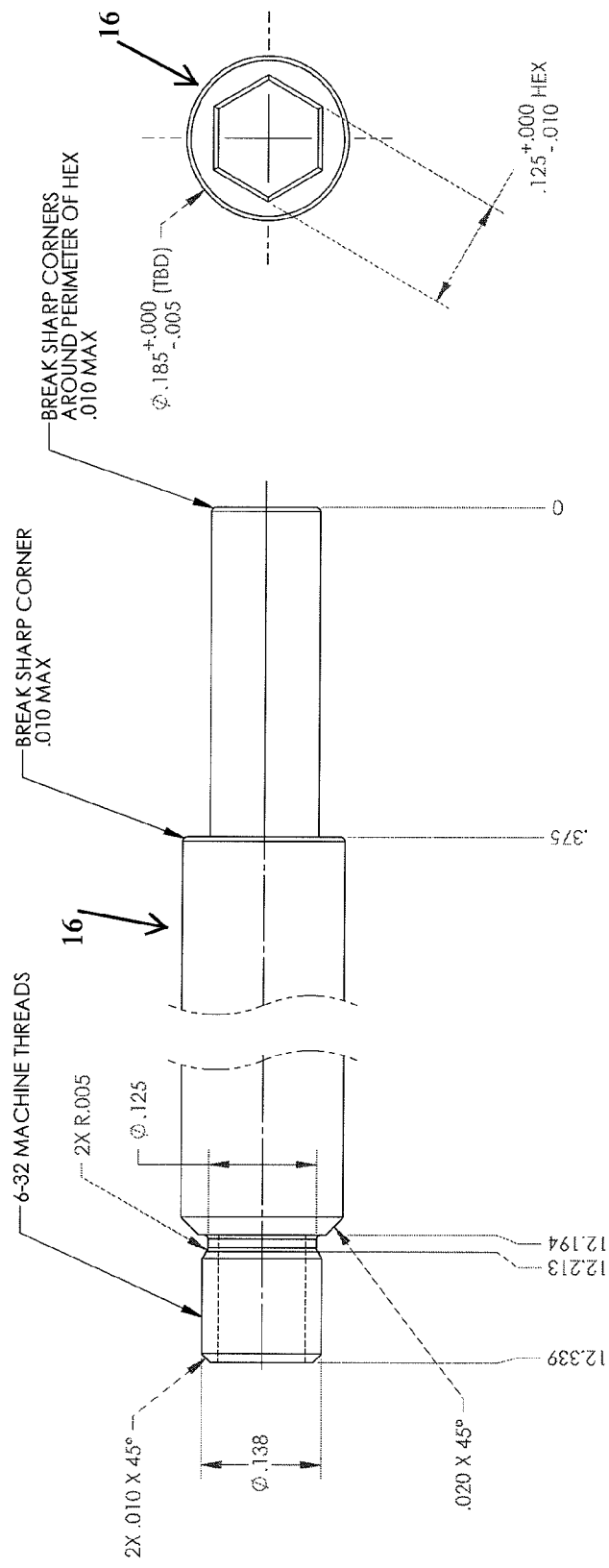

FIGS. 4A-21C illustrate more detailed views of the various components of the interbody insertion tool of FIG. 1, as well as embodiments of spinal cage assemblies that can be used with the interbody insertion tool. FIGS. 4A-4C are elevational views of a fixed tube welded component 1 illustrated in FIG. 1. FIG. 4D is a cross-sectional view of the component 1 taken along line A-A of FIG. 4C. FIGS. 5A and 5B are elevational views of an anterior inner rod component 2 illustrated in FIG. 1. FIGS. 6A-6D are elevational views of a main body component 2 illustrated in FIG. 1. FIGS. 6E and 6F are elevational views of the main body component 3 illustrated in FIG. 1. FIG. 6G is a cross-sectional view of the main body component 3 taken along line A-A of FIG. 6E. FIG. 6H is a detail view of section B of FIG. 6F. FIGS. 7A-7C are elevational views of a locking head component 4 illustrated in FIG. 1. FIG. 7D is a cross-sectional view of the locking head component 4 taken along line A-A of FIG. 7B. FIG. 7E is a detail view of section B of FIG. 7D. FIG. 7F is a perspective view of the locking head component 4 illustrated in FIG. 1. FIGS. 8A-8C are elevational views of a thumb roller component 5 illustrated in FIG. 1. FIG. 8D is a cross-sectional view of the thumb roller component 5 taken along line A-A of FIG. 8B. FIG. 8E is a perspective view of the thumb roller component 5 illustrated in FIG. 1. FIGS. 9A-9C are elevational views of an inner plug component 6 illustrated in FIG. 1. FIG. 9D is a cross-sectional view of the inner plug component 6 taken along line A-A of FIG. 9A. FIGS. 10A-10D are elevational views of a threaded T-handle component 10 illustrated in FIG. 1. FIG. 10E is a detail view of section A of FIG. 10C. FIG. 10F is a perspective view of the threaded T-handle component 10 illustrated in FIG. 1. FIGS. 11A and 11B are elevational views of a knurled nut component 12 illustrated in FIG. 1. FIG. 11C is a cross-sectional view of the knurled nut component 12 taken along line A-A of FIG. 11B. FIGS. 12A-12C are elevational views of an anterior insertion tool component 13 illustrated in FIG. 1. FIG. 12D is a cross-sectional view of the anterior insertion tool component 13 taken along line A-A of FIG. 12A. FIG. 12E is a cross-sectional view of the anterior insertion tool component 13 taken along line B-B of FIG. 12B. FIG. 12F is a cross-sectional view of the anterior insertion tool component 13 taken along line C-C of FIG. 12C. FIGS. 13A-13C are elevational views of a lateral insertion tool component 14 illustrated in FIG. 1. FIG. 13D is a cross-sectional view of the lateral insertion tool component 14 taken along line A-A of FIG. 13A. FIG. 13E is a cross-sectional view of the lateral insertion tool component 14 taken along line B-B of FIG. 13B. FIG. 13F is a cross-sectional view of the lateral insertion tool component 14 taken along line C-C of FIG. 13C. FIGS. 14A-14C are elevational views of an oblique insertion tool component 15 illustrated in FIG. 1. FIG. 14D is a cross-sectional view of the oblique insertion tool component 15 taken along line A-A of FIG. 14A. FIG. 14E is a cross-sectional view of the oblique insertion tool component 15 taken along line B-B of FIG. 14B. FIG. 14F is a cross-sectional view of the oblique insertion tool component 15 taken along line C-C of FIG. 14C. FIGS. 15A and 15B are elevational views of an oblique and lateral inner rod component 16 illustrated in FIG. 1.

Figure 16E:
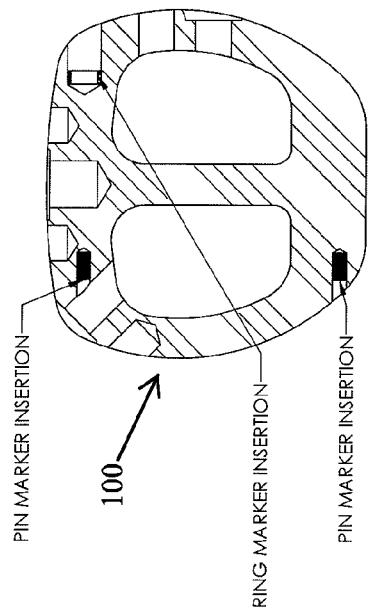
FIG. 16E is a cross-sectional view of the cage assembly taken along line A-A of FIG. 16B.
Figure 16B:
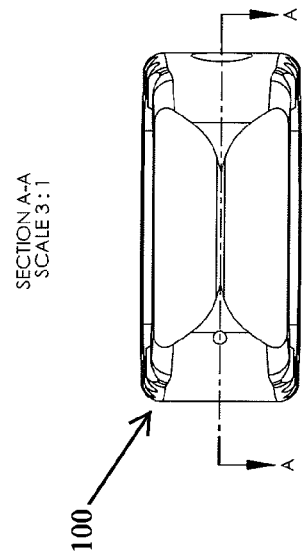
FIGS. 16B-16D are elevational views of the cage assembly of FIG. 16A.
Figure 16A:
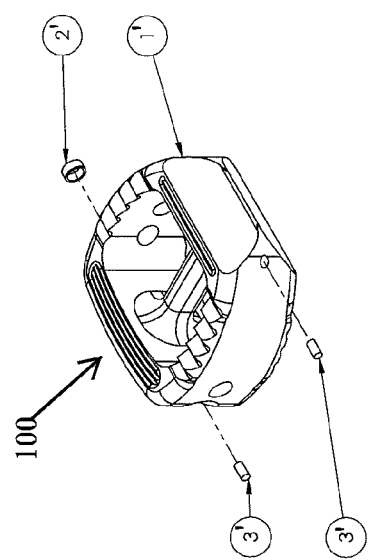
FIG. 16A is a perspective view of one embodiment of a spinal cage assembly for use with the interbody insertion tool of FIG. 1.
Figure 16C:
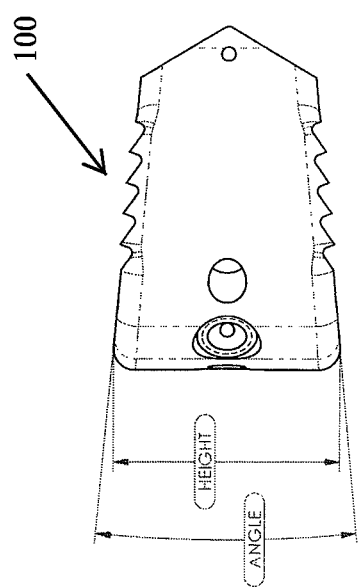
Figure 16D:
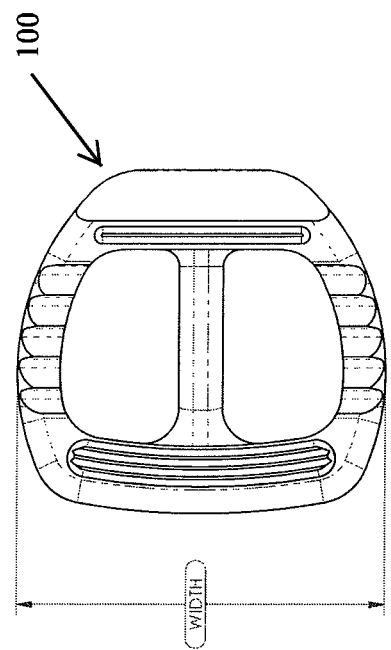
Figure 18B:
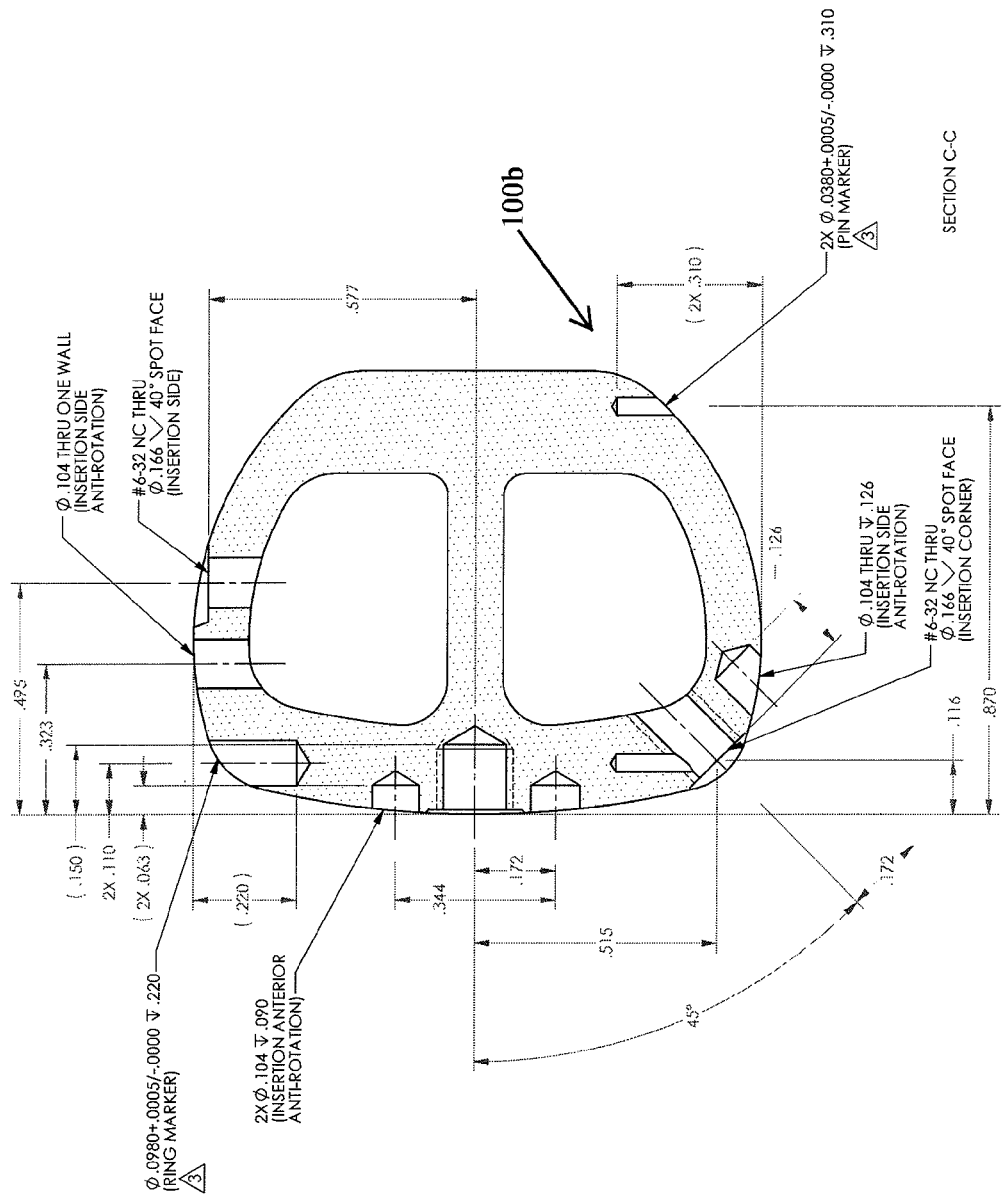
FIG. 18B is a cross-sectional view taken along line C-C of FIG. 18A.
Figure 18A:
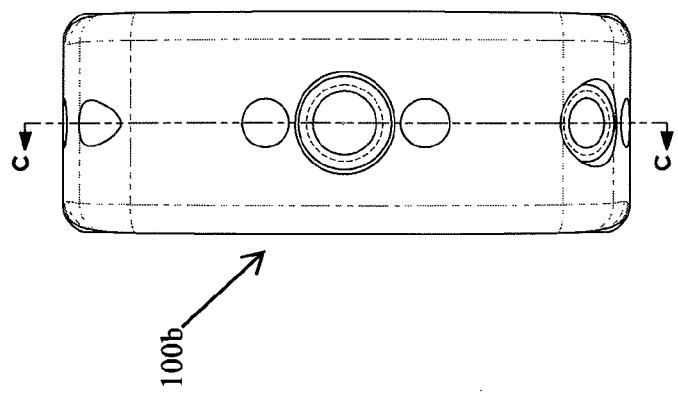
FIG. 18A is an elevational view of yet another embodiment of a spinal cage assembly for use with the interbody insertion tool of FIG. 1.

FIG. 16A is a perspective view of one embodiment of a spinal cage assembly 100 for use with the interbody insertion tool of FIG. 1. FIGS. 16B-16D are elevational views of the cage assembly 100 of FIG. 16A. FIG. 16E is a cross-sectional view of the cage assembly 100 taken along line A-A of FIG. 16B. FIGS. 16F-16J are elevational views of the cage assembly 100 of FIG. 16A. FIG. 16K is a cross-sectional view of the cage assembly 100 taken along line A-A of FIG. 16J. FIG. 16L is a detail view of section B of FIG. 16H. FIG. 17A is an elevational view of another embodiment of a spinal cage assembly 100a for use with the interbody insertion tool of FIG. 1. FIG. 17B is a cross-sectional view taken along line C-C of FIG. 17A. FIG. 18A is an elevational view of yet another embodiment of a spinal cage assembly 100b for use with the interbody insertion tool of FIG. 1. FIG. 18B is a cross-sectional view taken along line C-C of FIG. 18A. FIG. 19A is an elevational view of still another embodiment of a spinal cage assembly 100c for use with the interbody insertion tool of FIG. 1. FIG. 19B is a cross-sectional view taken along line D-D of FIG. 19A. FIG. 19C is a detail view of section G of FIG. 19B. FIG. 19D is a cross-sectional view taken along line E-E of FIG. 19A. FIG. 19E is a detail view of section F of FIG. 19D.

Figure 20B:
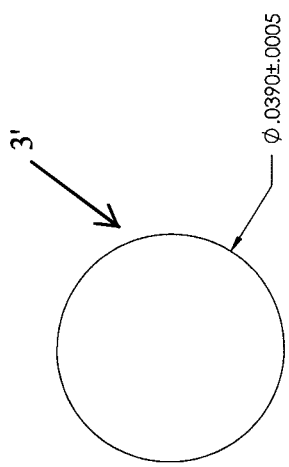
FIGS. 20B and 20C are perspective views of the marker pin of FIG. 20A.
Figure 20C:
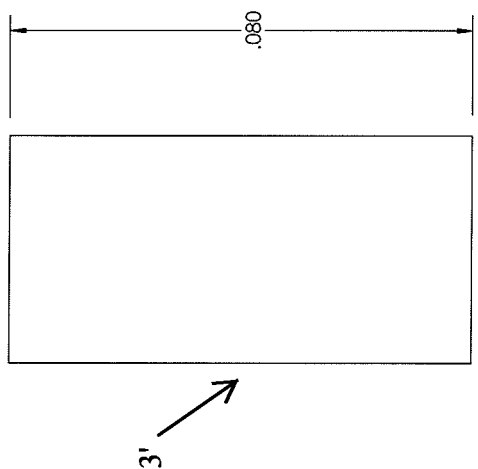
Figure 20A:
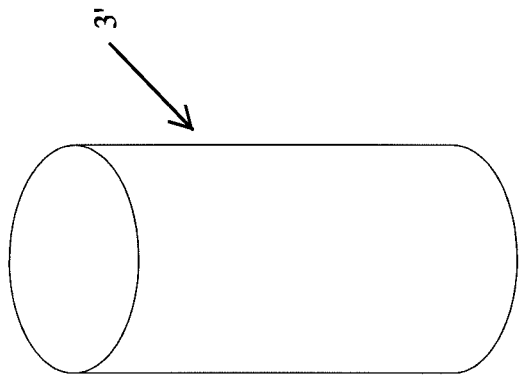
FIG. 20A is a perspective view of a spinal cage assembly marker pin according to one embodiment.
Figure 21B:
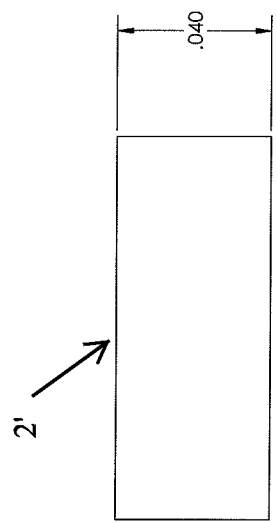
FIGS. 21B and 21C are perspective views of the marker ring of FIG. 21A.
Figure 21C:
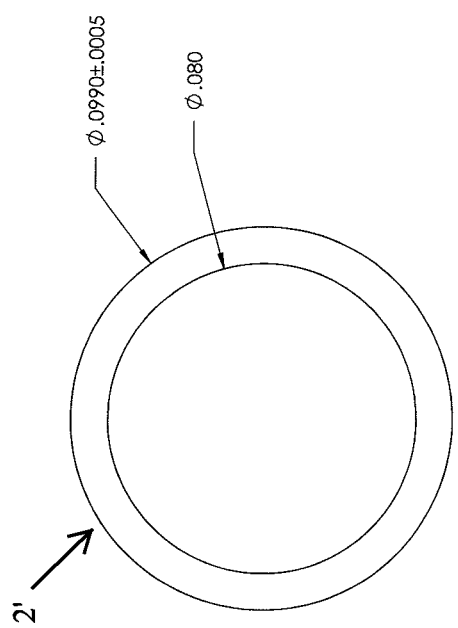
Figure 21A:
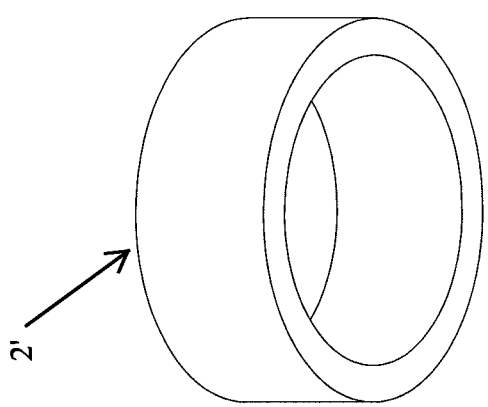
FIG. 21A is a perspective view of a spinal cage assembly marker ring according to one embodiment.

FIG. 20A is a perspective view of a spinal cage assembly marker pin 3' according to one embodiment. FIGS. 20B and 20C are perspective views of the marker pin 3' of FIG. 20A. FIG. 21A is a perspective view of a spinal cage assembly marker ring 2' according to one embodiment. FIGS. 21B and 21C are perspective views of the marker ring 2' of FIG. 21A.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. A device for inserting a spinal cage assembly between vertebral bodies during an interbody spinal fusion procedure, the device comprising:
   a handle portion disposed at a proximal end of the device, the handle portion comprising a body and a thumb roller rotatably attached to the body;
   a coupling portion attached to the handle portion; and
   a cage attachment portion at a distal end of the device, the cage attachment portion comprising an inner rod centrally located within the cage attachment portion, a proximal end of the inner rod engaging with the thumb roller such that rotation of the thumb roller relative to the body causes rotation of the inner rod, a distal end of the inner rod being configured to engage a spinal cage,
   wherein the coupling portion comprises:
      a fixed tube secured to the body of the handle portion, the inner rod of the cage attachment portion extending through the fixed tube; and
      a locking mechanism spaced apart from the thumb roller and secured to the fixed tube, the locking mechanism being selectively configurable between a coupling position and a locked position, wherein:
      in the locked position, the locking mechanism secures the inner rod within the fixed tube; and
      in the coupling position, the inner rod is unsecured to the fixed tube and the inner rod can be freely separated from the thumb roller while the thumb roller remains rotatably secured to the body so that rotation of the thumb roller relative to the body does not cause rotation of the inner rod.

2. The device of claim 1, wherein rotation of the inner rod causes the inner rod to disengage with an engaged spinal cage.

3. The device of claim 1, wherein the thumb roller further comprises a cavity, at least a portion of the inner rod being disposed within the cavity of the thumb roller.

4. The device of claim 1, wherein the coupling portion further comprises a spring disposed at least partially between the handle portion and the locking mechanism, the spring biasing the locking mechanism into the locked position.

5. The device of claim 4, wherein the locking mechanism comprises:
   a locking head disposed about the fixed tube, the fixed tube extending at least partially within the locking head, the inner rod extending through the fixed tube and the locking head; and
   one or more locking balls disposed at an interface between the fixed tube and the locking head, wherein in the locked position, the locking head depresses the one or more locking balls, thereby securing the inner rod within the fixed tube.

6. The device of claim 1, wherein the body having:
   an outer gripping surface and an inner surface cavity, the thumb roller being disposed at least partially within the inner surface cavity; and
   at least one opening extending from the outer gripping surface to the inner surface cavity such that a portion of the thumb roller is accessible through the at least one opening.

7. The device of claim 6, wherein the handle portion further comprises:
   a proximal axial opening for receiving at least a portion of the thumb roller into the inner surface cavity; and
   a distal axial opening for receiving at least a portion of the inner rod into the inner surface cavity.

8. The device of claim 1, wherein the inner rod is cannulated to provide a fluidic connection between the inner rod and an engaged spinal cage.

9. A system, comprising:
   the device of claim 1; and
   a spinal cage assembly attached to the distal end of the inner rod.

10. A device for inserting a spinal cage assembly between vertebral bodies during an interbody spinal fusion procedure, the device comprising:
    a handle portion comprising: (i) a body having an outer gripping surface and an inner surface cavity, and (ii) a thumb roller disposed at least partially within the inner surface cavity and being rotatable relative to the body, the body having at least one opening extending from the outer gripping surface to the inner surface cavity such that a portion of the thumb roller is accessible through the at least one opening;
    a coupling portion attached to the handle portion, the coupling portion comprising:
       a fixed tube secured to the handle portion; and
       a locking mechanism spaced apart from the thumb roller and secured to the fixed tube, the locking mechanism being selectively configurable between a coupling position and a locked position; and a cage attachment portion comprising: (i) an outer insertion tool and (ii) an inner rod extending through the outer insertion tool such that the inner rod extends at least partially into the inner surface cavity of the body of the handle, the coupling portion being disposed at least partially between the handle and the outer insertion tool of the cage attachment portion, the inner rod extending through the fixed tube of the coupling portion, a proximal end of the inner rod engaging with the thumb roller such that rotation of the thumb roller within the inner surface cavity causes rotation of the inner rod, a distal end of the inner rod being configured to engage a spinal cage, wherein:

in the locked position, the locking mechanism secures the inner rod within the fixed tube;

in the coupling position, the inner rod is unsecured to the fixed tube; and rotation of the inner rod causes the inner rod to disengage with an engaged spinal cage.

11. A method for inserting a spinal cage between vertebral bodies during an interbody spinal fusion procedure, the method comprising:

attaching a device to the spinal cage, the device comprising:
- a handle portion disposed at a proximal end of the device, the handle portion comprising a body and a thumb roller rotatable relative to the body;
- a coupling portion attached to the handle portion, the coupling portion comprising a locking mechanism; and
- a cage attachment portion at a distal end of the device, the cage attachment portion comprising an inner rod centrally located within the cage attachment portion, a proximal end of the inner rod engaging with the thumb roller such that rotation of the thumb roller relative to the body causes rotation of the inner rod, the spinal cage being attached to a distal end of the inner rod;

inserting the spinal cage between the vertebral bodies using the handle portion of the device;

decoupling the handle portion of the device from the spinal cage by moving the locking mechanism of the coupling portion of the device into a coupling position; and moving the handle portion away from the spinal cage such that the inner rod of the cage attachment portion of the device remains engaged with the spinal cage upon movement of the handle portion away from the spinal cage.

12. The method of claim 11, further comprising inserting the proximal end of the inner rod through an outer insertion tool of the cage attachment portion such that the inner rod engages with the thumb roller of the handle portion of the device.

13. The method of claim 12, wherein the spinal cage is rotationally attached to the distal end of inner rod, the method further comprising rotating the thumb roller of the handle portion of the device in a first direction thereby detaching the spinal cage from the inner rod.

14. The method of claim 13, wherein attaching the device to the spinal cage comprises rotating the thumb roller of the handle portion of the device in a second direction.

15. The method of claim 11, further comprising securing the spinal cage to one or more of the vertebral bodies.

* * * * *